(12) United States Patent
Lintula et al.

(10) Patent No.: US 12,396,768 B2
(45) Date of Patent: Aug. 26, 2025

(54) INTRAMEDULLARY NAIL ALIGNMENT GUIDES, FIXATION GUIDES, DEVICES, SYSTEMS, AND METHODS OF USE

(71) Applicant: Paragon 28, Inc., Englewood, CO (US)

(72) Inventors: Eric Lintula, Parker, CO (US); Albert Dacosta, Lone Tree, CO (US); Randy Allard, Golden, CO (US); Frank S. Bono, Castle Rock, CO (US); Spanky Raymond, Uniontown, OH (US)

(73) Assignee: Paragon 28, Inc., Englewood, CO (US)

( * ) Notice: Subject to any disclaimer, the term of this patent is extended or adjusted under 35 U.S.C. 154(b) by 79 days.

(21) Appl. No.: 18/329,829

(22) Filed: Jun. 6, 2023

(65) Prior Publication Data

US 2023/0310011 A1     Oct. 5, 2023

Related U.S. Application Data

(60) Continuation of application No. 17/248,165, filed on Jan. 12, 2021, now Pat. No. 11,666,345, which is a
(Continued)

(51) Int. Cl.
*A61B 17/72*     (2006.01)
*A61B 17/17*     (2006.01)

(52) U.S. Cl.
CPC ...... *A61B 17/7291* (2013.01); *A61B 17/1717* (2013.01); *A61B 17/1725* (2013.01); *A61B 17/1775* (2016.11); *A61B 17/72* (2013.01)

(58) Field of Classification Search
CPC . A61B 17/72; A61B 17/7208; A61B 17/7216; A61B 17/7225; A61B 17/7233;
(Continued)

(56) References Cited

U.S. PATENT DOCUMENTS

| 5,429,641 A | 7/1995 | Gotfried |
| 6,692,496 B1 | 2/2004 | Wardlaw |

(Continued)

FOREIGN PATENT DOCUMENTS

| CN | 102639074 B | * 3/2016 | ......... A61B 17/7225 |
| EP | 2967686 B1 | * 9/2023 | ......... A61B 17/1717 |

(Continued)

OTHER PUBLICATIONS

Budny et al. "Naviculocuneiform Arthrodesis," Clinics in Podiatric Medicine and Surgery, vol. 24, pp. 753-763, Oct. 2007.
(Continued)

*Primary Examiner* — Eric S Gibson
(74) *Attorney, Agent, or Firm* — Heslin Rothenberg Farley & Mesiti P.C.; Jacquelyn A. Graff, Esq.

(57) ABSTRACT

Alignment guide systems, fixation guide devices, and methods for positioning and inserting an intramedullary nail are disclosed. The alignment guide system includes a targeting guide with a first end and a second end, an alignment wire rotatably engaging a second end of the targeting guide, and a guide sleeve insert engaging an opening in the first end of the targeting guide. The fixation guide device including a frame including a first end and a second end, a compression device slidingly coupled to the first end of the frame, and the intramedullary nail secured to a nail attachment apparatus of the frame. A method of inserting an intramedullary nail into two bones for fixation of the two bones is also disclosed.

11 Claims, 30 Drawing Sheets

Related U.S. Application Data division of application No. 15/907,850, filed on Feb. 28, 2018, now Pat. No. 10,888,338, which is a continuation of application No. PCT/US2018/020046, filed on Feb. 27, 2018.

(60) Provisional application No. 62/464,175, filed on Feb. 27, 2017.

(58) Field of Classification Search
CPC .............. A61B 17/7241; A61B 17/725; A61B 17/7283; A61B 17/7291
See application file for complete search history.

(56) References Cited

U.S. PATENT DOCUMENTS

| | | | |
|---|---|---|---|
| 7,785,326 B2 | 8/2010 | Green | |
| 7,819,877 B2 | 10/2010 | Guzman | |
| 8,206,389 B2 | 6/2012 | Huebner | |
| 9,241,744 B2 | 1/2016 | Blake | |
| 9,662,221 B2 * | 5/2017 | Surma | A61B 17/739 |
| 9,907,562 B2 * | 3/2018 | DaCosta | A61B 17/1717 |
| 10,888,338 B2 * | 1/2021 | Lintula | A61B 17/72 |
| 10,987,146 B2 * | 4/2021 | Denham | A61B 17/7291 |
| 11,179,166 B2 * | 11/2021 | Dacosta | A61B 17/1725 |
| 11,666,345 B2 * | 6/2023 | Lintula | A61B 17/1725 606/62 |
| 2003/0009217 A1 | 1/2003 | McKernan | |
| 2005/0033301 A1 | 2/2005 | Lombardo | |
| 2006/0015188 A1 | 1/2006 | Grimes | |
| 2006/0189996 A1 | 8/2006 | Orbay | |
| 2007/0225714 A1 | 9/2007 | Gradl | |
| 2009/0036931 A1 | 2/2009 | Pech | |
| 2009/0062797 A1 | 3/2009 | Huebner | |
| 2010/0121324 A1 | 5/2010 | Tyber | |
| 2011/0282397 A1 | 11/2011 | Richter | |
| 2012/0109217 A1 | 5/2012 | Perineau | |
| 2012/0209268 A1 | 8/2012 | Overes | |
| 2012/0303038 A1 | 11/2012 | Durante | |
| 2013/0046311 A1 | 2/2013 | Blake | |
| 2013/0150903 A1 | 6/2013 | Sammarco | |
| 2013/0325076 A1 * | 12/2013 | Palmer | A61B 17/8635 606/104 |
| 2013/0331947 A1 * | 12/2013 | Surma | A61B 17/1725 606/99 |
| 2015/0032168 A1 | 1/2015 | Orsak | |
| 2015/0150683 A1 | 6/2015 | Donner | |
| 2015/0245923 A1 | 9/2015 | Abdou | |
| 2015/0342659 A1 | 12/2015 | Limouze | |
| 2016/0030064 A1 * | 2/2016 | Dacosta | A61B 17/1775 606/105 |
| 2016/0166264 A1 | 6/2016 | Ritchey | |
| 2017/0189085 A1 | 7/2017 | Krause | |
| 2017/0216043 A1 * | 8/2017 | Surma | A61F 2/4261 |
| 2018/0193039 A1 * | 7/2018 | Dacosta | A61B 17/1775 |
| 2018/0242987 A1 * | 8/2018 | Lintula | A61B 17/1717 |
| 2018/0242988 A1 | 8/2018 | Dacosta | |
| 2018/0280069 A1 | 10/2018 | Barmes | |
| 2019/0038326 A1 | 2/2019 | Hedgeland | |
| 2021/0128177 A1 * | 5/2021 | Lintula | A61B 17/1717 |
| 2022/0079607 A1 * | 3/2022 | Dacosta | A61B 17/1775 |
| 2023/0310011 A1 * | 10/2023 | Lintula | A61B 17/72 606/62 |

FOREIGN PATENT DOCUMENTS

| | | | | |
|---|---|---|---|---|
| EP | 4260820 A2 * | 10/2023 | ......... | A61B 17/1717 |
| EP | 3585287 B1 * | 11/2024 | ......... | A61B 17/1717 |
| EP | 4480427 A2 * | 12/2024 | ......... | A61B 17/1717 |
| ES | 2959525 T3 * | 2/2024 | ......... | A61B 17/1717 |
| JP | 2009112594 | 5/2009 | | |
| WO | 1994015556 | 7/1994 | | |
| WO | 2009052294 | 4/2009 | | |
| WO | 2012103335 | 8/2012 | | |
| WO | WO-2014152219 A2 * | 9/2014 | ......... | A61B 17/1717 |
| WO | WO-2018157168 A1 * | 8/2018 | ......... | A61B 17/1717 |

OTHER PUBLICATIONS

Kamat et al. "Laparoscopic extraction of fractured Kirschner wire from the pelvis," Journal of Minimal Access Surgery, vol. 10, No. 2, pp. 97-98, Jun. 2014.

* cited by examiner

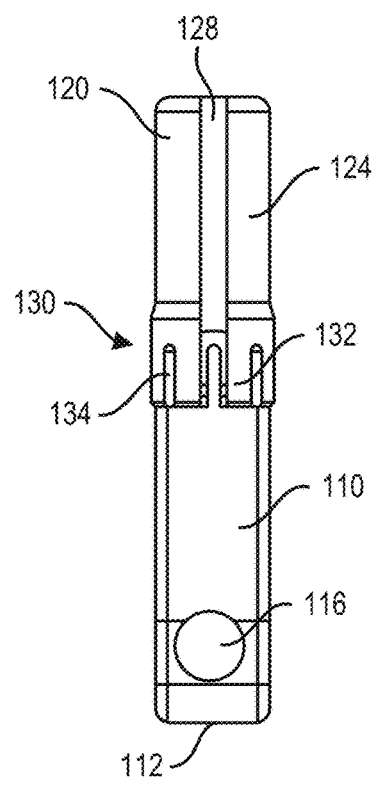 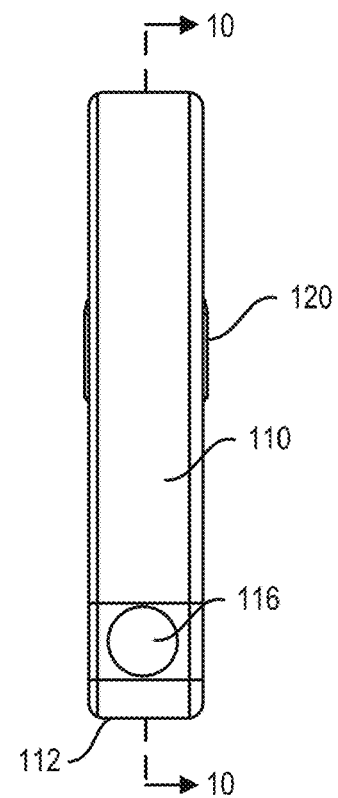
FIG. 8    FIG. 9
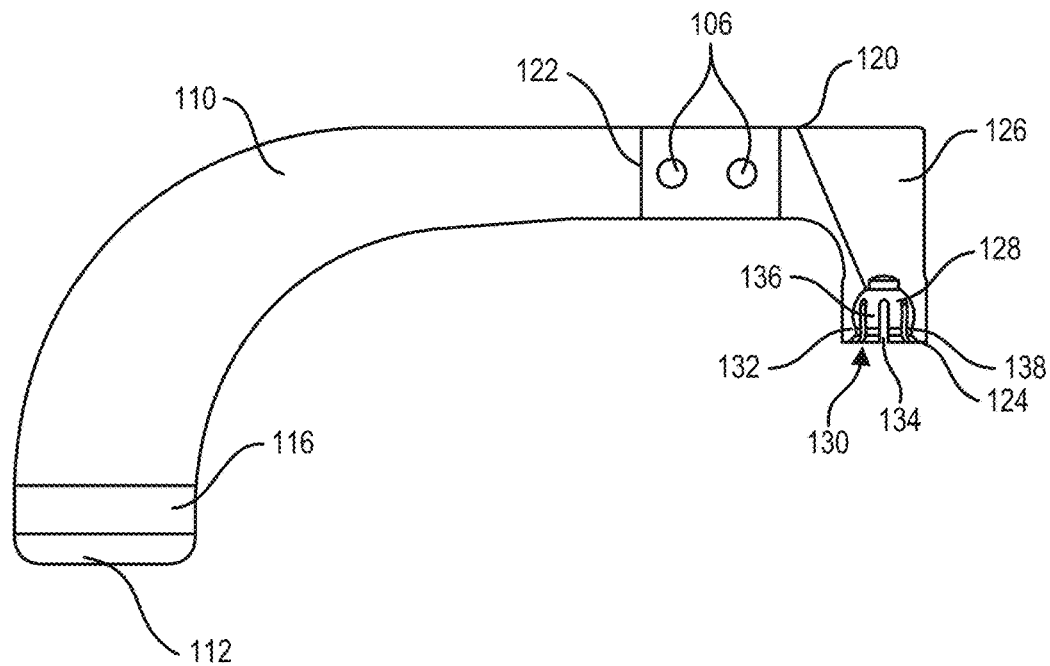
FIG. 10

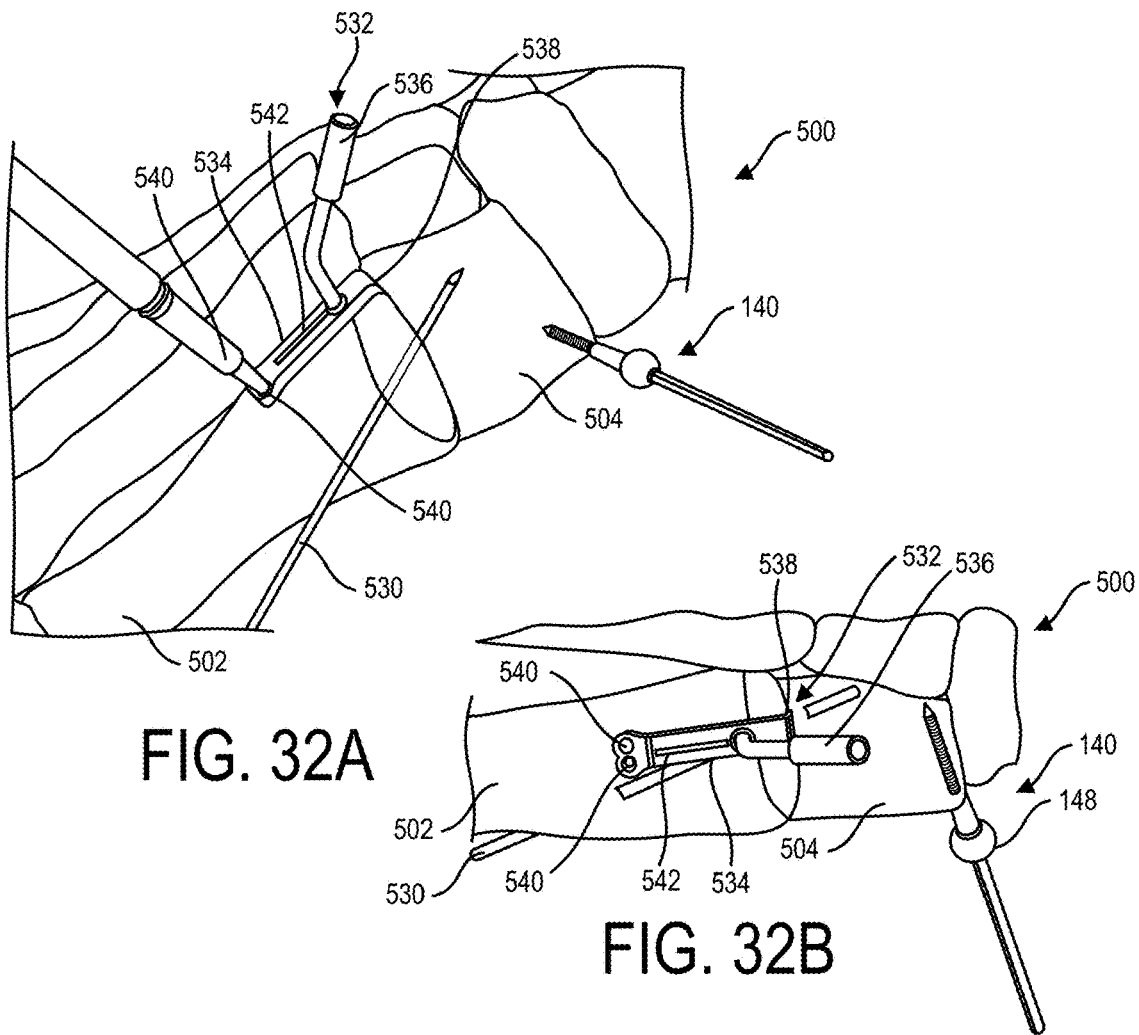
FIG. 32A
FIG. 32B
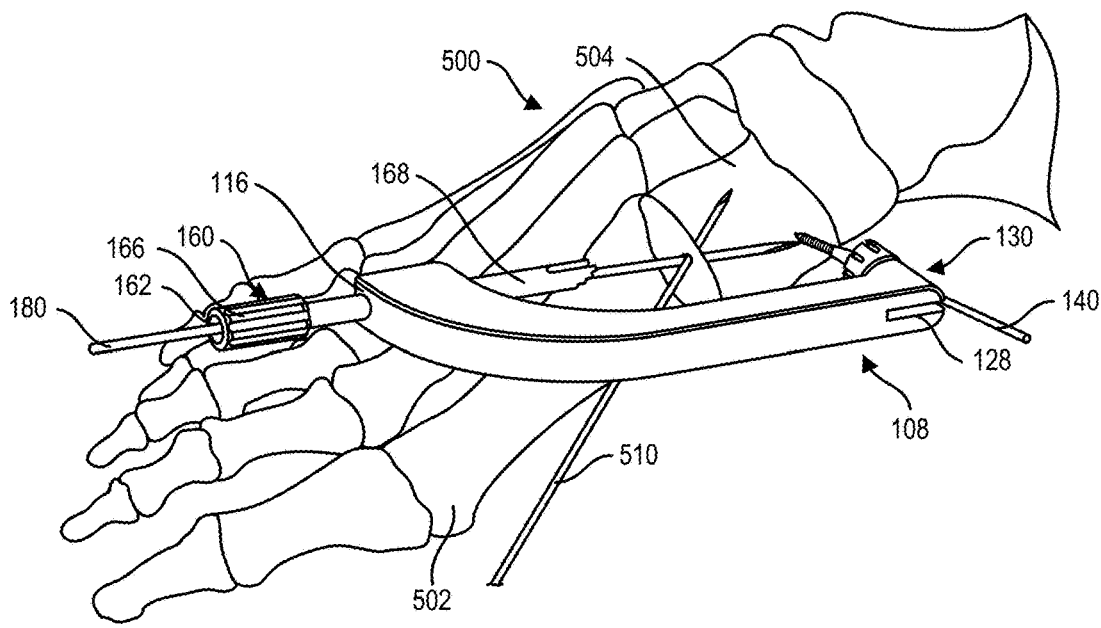
FIG. 33

INTRAMEDULLARY NAIL ALIGNMENT GUIDES, FIXATION GUIDES, DEVICES, SYSTEMS, AND METHODS OF USE

CROSS-REFERENCE TO RELATED APPLICATION

This application is a continuation of U.S. application Ser. No. 17/248,165 filed on Jan. 12, 2021, which issued as U.S. Pat. No. 11,666,345 on Jun. 6, 2023, which is a divisional of U.S. application Ser. No. 15/907,850 filed on Feb. 28, 2018, which issued as U.S. Pat. No. 10,888,338 on Jan. 12, 2021, which is a continuation of PCT Application No. PCT/US2018/020046 filed on Feb. 27, 2018, which claims priority benefit under 35 U.S.C. § 119(e) of U.S. provisional application No. 62/464,175 filed Feb. 27, 2017, which are incorporated herein by reference in their entireties.

TECHNICAL FIELD

The present invention relates generally to general surgery, podiatric, and orthopaedic related to fixation of prepared joint surfaces. More specifically, but not exclusively, the present invention relates to implants, guides, devices, instruments, systems and methods for fixing a joint using an intramedullary nail.

BACKGROUND OF THE INVENTION

The current technology for fusions across two bones utilizes plate and screw fixation that can only be applied on the approach surface. Since the plates are attached outside the fusion zone, the plates will experience bending moments and are limited in their ability to provide uniform compression forces across the fusion site or surfaces. In addition, the plates and screws may create pain due to hardware prominence on the patient's bones. Further, the blood supply to the periosteum may be compromised by attaching a plate to the exterior surface of the bones. Current medial plating systems may experience recurrent hallux valgus and dorsal plating systems may experience plantar gapping over time.

Accordingly, new and improved intramedullary nail alignment guides, fixation guides, devices, and methods which overcome the above-referenced problems and others are needed.

SUMMARY OF THE INVENTION

The present invention is directed toward devices and methods for use in fixation of a patient's joints or for fixation of a fracture. The alignment and fixation guides provide an orientation for insertion of intramedullary nails through a patient's joint or fracture.

In one aspect of the present invention provided herein, is a fixation system. The fixation system including an alignment guide system for forming an opening across a joint and a fixation guide device for inserting an intramedullary nail into the opening.

In another aspect of the present invention provided herein, is an alignment guide system. The alignment guide system including a targeting guide with a first end and a second end, an alignment wire rotatably engaging a second end of the targeting guide, and a guide sleeve insert engaging an opening in the first end of the targeting guide.

In yet another aspect of the present invention provided herein, is a fixation guide device for positioning and inserting an intramedullary nail. The fixation guide device including a frame including a first end and a second end, a compression device slidingly coupled to the first end of the frame, and the intramedullary nail secured to a nail attachment apparatus of the frame.

In a further aspect of the present invention provided herein, is a method of inserting an intramedullary nail into two bones for fixation of the two bones. The method may include creating an incision near the two bones and preparing the two bones for fixation. The method may also include securing an alignment guide to at least one of the two bones to position a guidewire across the two bones and removing the alignment guide from the at least one of the two bones. In addition, the method may include drilling over the guidewire to create a cavity for the intramedullary nail that passes through the two bones, wherein the intramedullary nail includes a securing screw hole at a first end of the intramedullary nail and at least two peg holes. The method may further include obtaining a fixation guide device, wherein the fixation guide device includes a frame with at least two drill holes and a compression device. The method may also include attaching the intramedullary nail to the compression device of the fixation guide device and inserting the intramedullary nail into the cavity. Further, the method may include inserting at least one peg into a first bone of the two bones and through at least one first opening in the intramedullary nail and using the at least one first peg and compression device to compress the two bones. The method may also include inserting at least one second peg into a second bone of the two bones and through at least one second opening in the intramedullary nail to secure the two bones in compression and detaching the intramedullary nail from the fixation guide and removing the fixation guide device. In addition, the method may include inserting a locking screw into the securing screw hole. Finally, the method may include closing the incision.

These and other objects, features and advantages of this invention will become apparent from the following detailed description of the various aspects of the invention taken in conjunction with the accompanying drawings.

BRIEF DESCRIPTION OF THE DRAWINGS

The accompanying drawings, which are incorporated in and constitute a part of the specification, illustrate embodiments of the invention and together with the detailed description herein, serve to explain the principles of the invention. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the invention.

FIG. 8 is a proximal view of the implant alignment guide system of FIG. 3, in accordance with an aspect of the present invention;

FIG. 9 is a distal view of the implant alignment guide system of FIG. 3, in accordance with an aspect of the present invention;

FIG. 10 is a cross-sectional view of the implant alignment guide of FIG. 1 taken along line 10-10 in FIG. 9, in accordance with an aspect of the present invention;

FIG. 32A is a perspective view of the embodiment of FIG. 31 with a nail positioning guide positioned on the patient's foot, in accordance with an aspect of the present invention;

FIG. 32B is a top view of the embodiment of FIG. 32A, in accordance with an aspect of the present invention;

FIG. 33 is a perspective side view of the embodiment of FIG. 31 with the alignment guide system of FIG. 1 positioned on the foot and engaging the sphere wire, in accordance with an aspect of the present invention;

DETAILED DESCRIPTION FOR CARRYING OUT THE INVENTION

Figure 1:
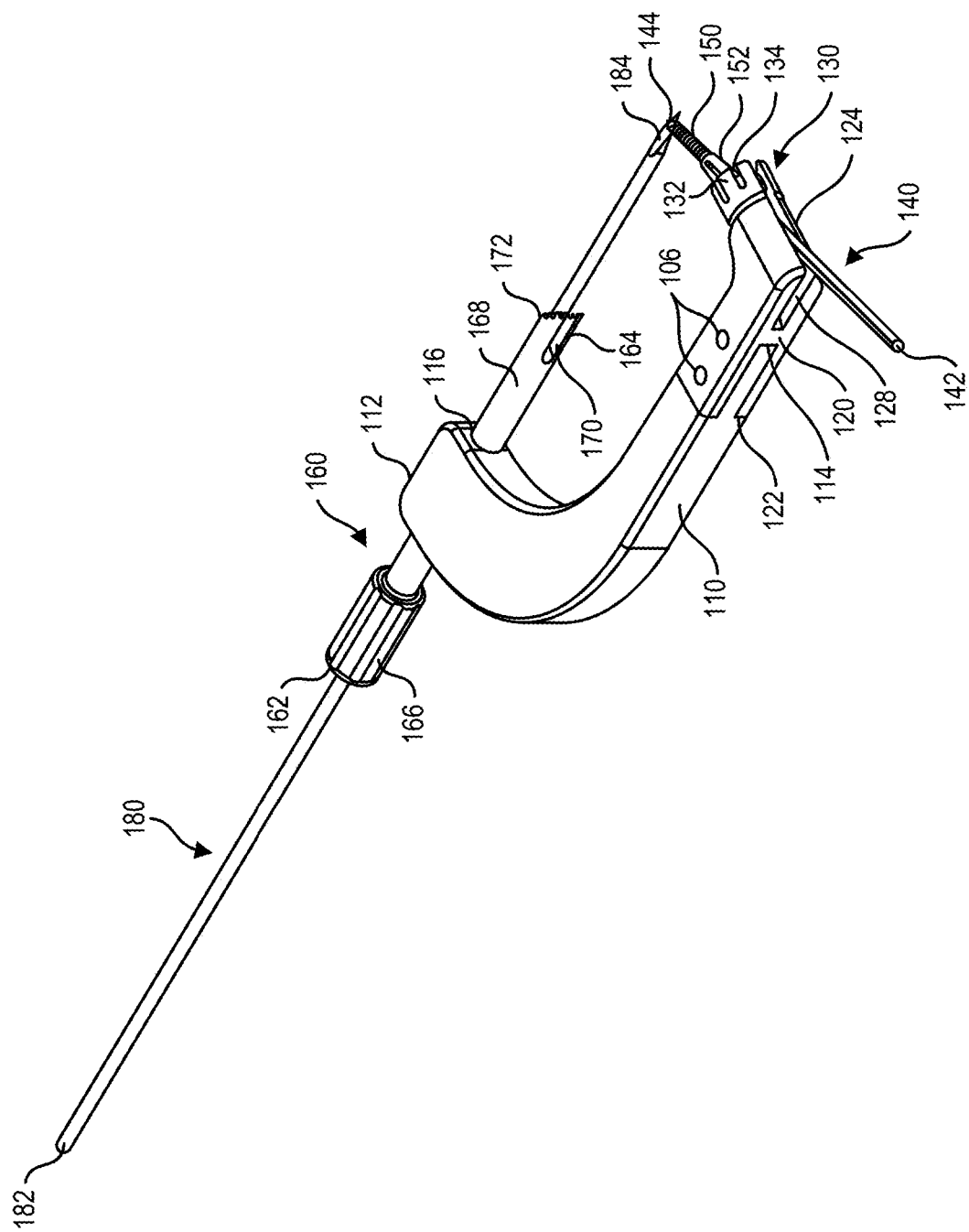
FIG. 1 is a perspective view from a lateral side of one embodiment of an implant alignment guide system, in accordance with an aspect of the present invention.

Generally stated, disclosed herein are implants, guides, devices, instruments, and systems for fixing a joint using an intramedullary nail. Further, methods for implanting and removing an intramedullary nail using the implants, guides, devices, instruments and systems are discussed.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current implants, devices, instrumentation and methods are described herein with reference to use with the bones of the foot, the bones of the foot, ankle and lower leg may be used to describe the surfaces, positions, directions or orientations of the implants, devices, instrumentation and methods. Further, the implants, devices, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the implants, devices, instrumentation and methods, and the aspects, components, features and the like thereof, described herein with respect to the right foot may be mirrored so that they likewise function with the left foot. Further, the implants, devices, instrumentation and methods, and the aspects, components, features and the like thereof, disclosed herein are described with respect to the foot for brevity purposes, but it should be understood that the implants, devices, instrumentation and methods may be used with other bones of the body having similar structures.

Referring to the drawings, wherein like reference numerals are used to indicate like or analogous components throughout the several views, and with particular reference to FIGS. 1-10, there is illustrated an exemplary embodiment of an alignment guide system 100. The alignment guide system 100 includes an alignment guide or polyaxial targeting guide 108, a pivoting member 140, a guide sleeve insert 160, and a guide wire or k-wire 180. The alignment guide or polyaxial targeting guide 108 includes a body 110 and a pivot assembly 120. The body 110 having a first end 112 and a second end 114. The first end 112 includes a first opening 116 for receiving the guide sleeve insert 160. The first opening 116 may extend entirely through the first end 112 of the body 110 along a longitudinal axis of the alignment guide 108. The second end 114 includes a coupling region 118 and second openings (not shown) extending through the coupling region 118. The coupling region 118 may have a width or thickness smaller than the width or thickness of the rest of the body 110. The second openings may be sized and shaped for receiving fasteners 106 to couple the body 110 to the pivot assembly 120. The body 110 may also have, for example, a curvature or arc as the body extends from the first end 112 to the second end 114. The curvature may be positioned, for example, near the distal or first end 112 of the alignment guide 108.

Figure 2:
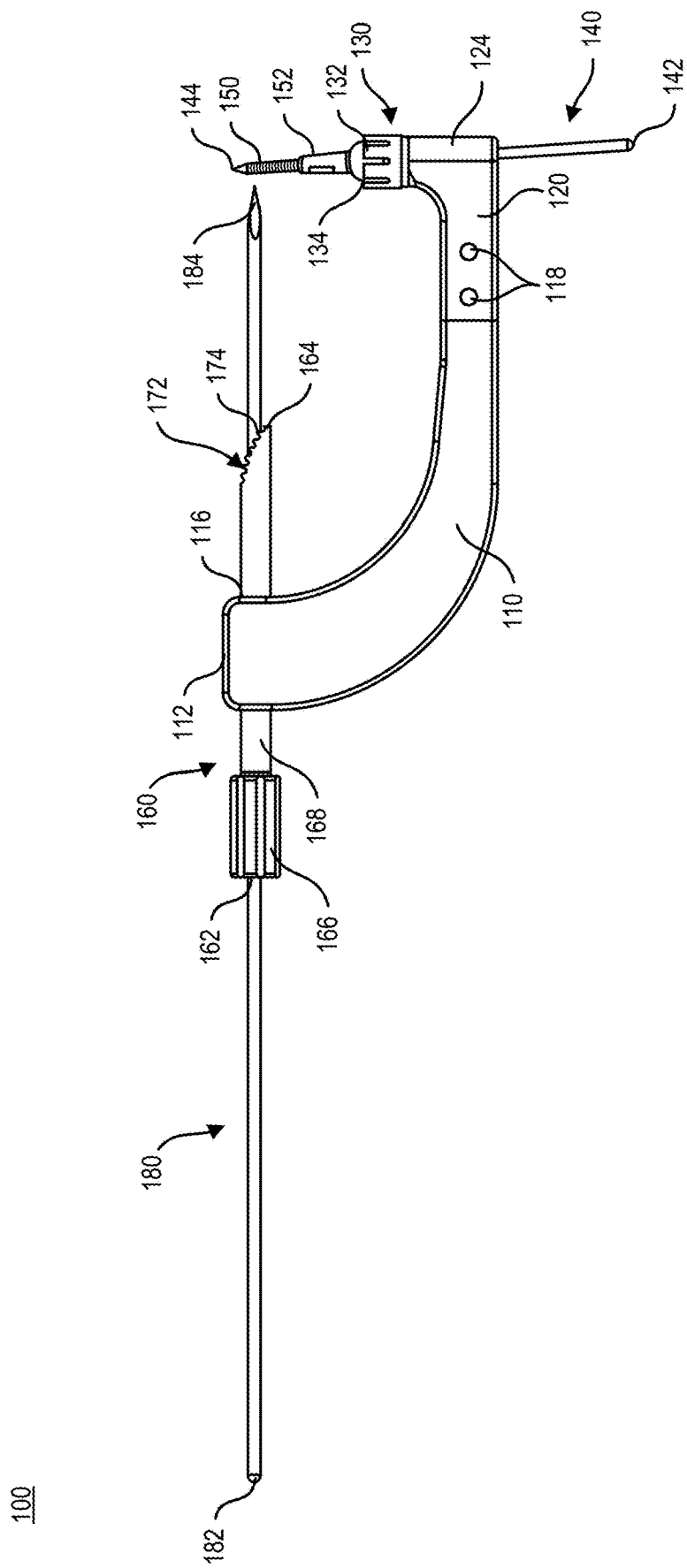
FIG. 2 is a top view of the implant alignment guide system of FIG. 1, in accordance with an aspect of the present invention.
Figure 3:
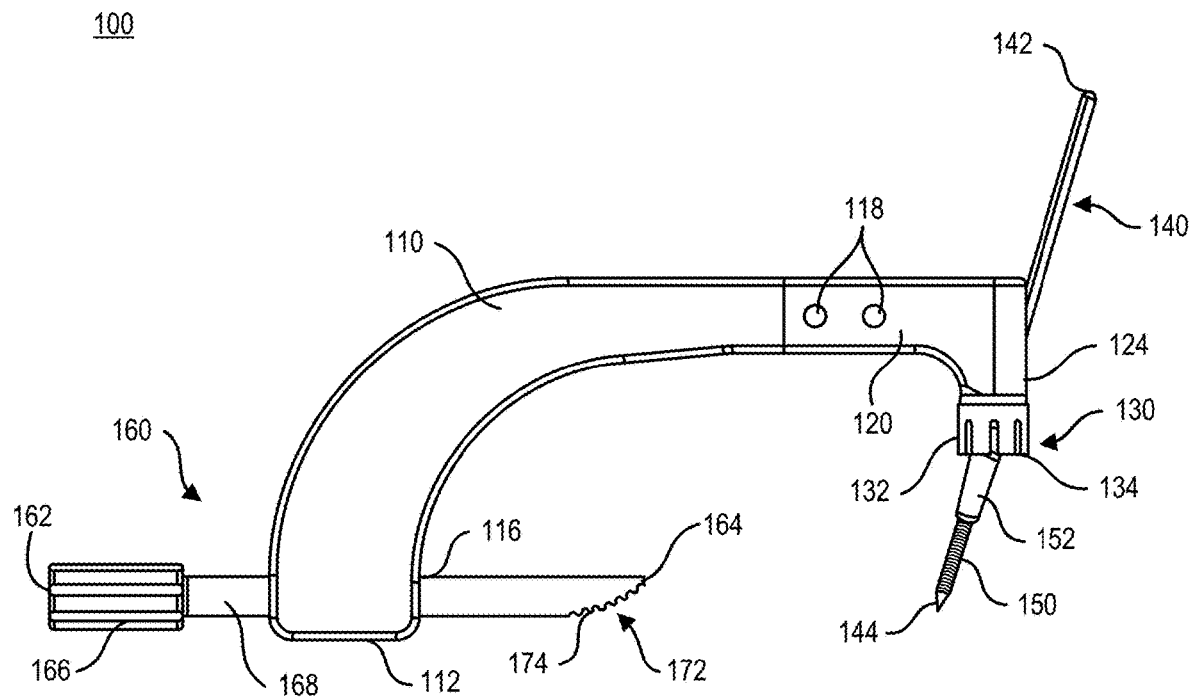
FIG. 3 is a top view of a portion of the implant alignment guide system of FIG. 1, in accordance with an aspect of the present invention.
Figure 4:
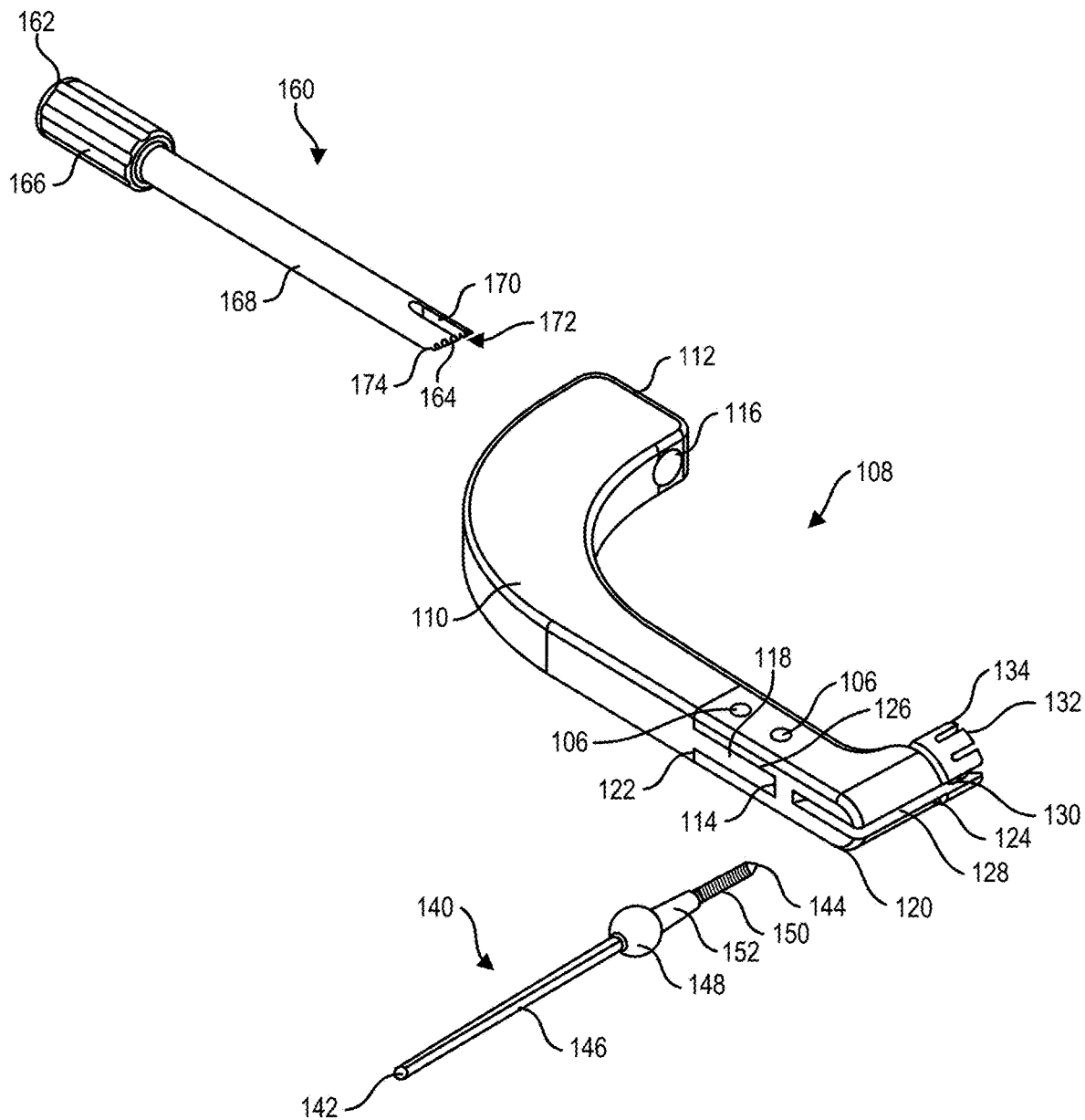
FIG. 4 is an exploded, top perspective view of the implant alignment guide system of FIG. 3, in accordance with an aspect of the present invention.
Figure 5:
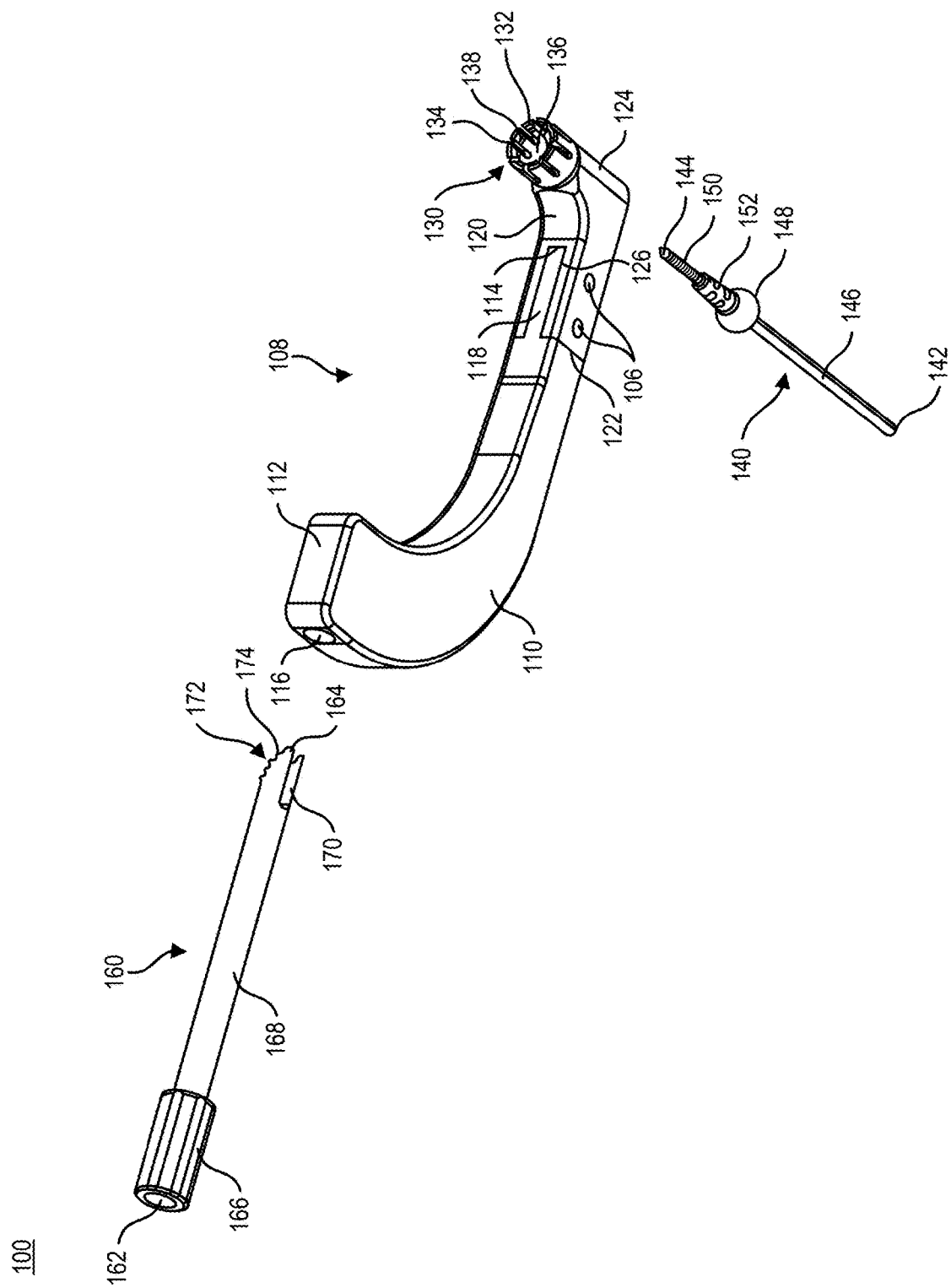
FIG. 5 is an exploded, side perspective view of the implant alignment guide system of FIG. 3, in accordance with an aspect of the present invention.

As shown in FIGS. 1-8 and 10, the pivot assembly 120 includes a first end 122 and a second end 124. The first end 122 includes a first slot 126 inset into the first end 122 for receiving the coupling region 118 at the second end 114 of the body 110. The second end 124 includes a pivot slot 128 and a pivoting end 130 for receiving the pivoting member 140. As shown in FIG. 10, the pivot slot 128 may be angled, for example, along the longitudinal axis of the alignment guide 108. The pivot slot 128 may be, for example, narrower on the medial side than the lateral side of the alignment guide 108. The pivoting end 130 may include, for example, a plurality of teeth, protrusions, or extension members 132 alternating with a plurality of grooves or reliefs 134 around the circumference of the pivoting end 130. Each of the plurality of teeth 132 may be, for example, curved on the interior surface of the pivoting end 130 to form a curved region 136. The curved regions 136 on each of the plurality of teeth 132 may form a spherical opening or opening with a circular or round cross-section on the interior surface of the pivoting end 130. The plurality of teeth 132 may also include, for example, a projection or extension 138 positioned near the second end 124 of the pivoting assembly 120 and extending into the spherical opening formed by the curved regions 136 of the teeth 132. The projections 138 provide a retaining surface for coupling the pivoting member 140 to the alignment guide 108, as shown in FIGS. 1-3.

The pivoting member 140 may include a first end 142 and a second end 144, as shown in FIGS. 4-7. The terms "pivoting member," "sphere wire," "grip wire," and "alignment wire" may be used interchangeably herein as the each essentially refer to a wire including a protrusion. The pivoting member 140 may also include a wire portion 146 extending from the first end 142 to a pivot protrusion or spherical member 148. The pivot protrusion 148 may be, for example, spherical or may have a circular or round cross-section and be sized and shaped to match the opening between the plurality of teeth 132 of the pivoting end 130. The pivot protrusion 148 may rotate within the plurality of teeth 132 in the pivoting end 130. The pivoting member 140 may also include an insertion end 150 and a tapered region 152 extending between the pivot protrusion 148 and the insertion end 150. The insertion end 150 may have a pointed tip for insertion into the patient's foot.

Figure 6:
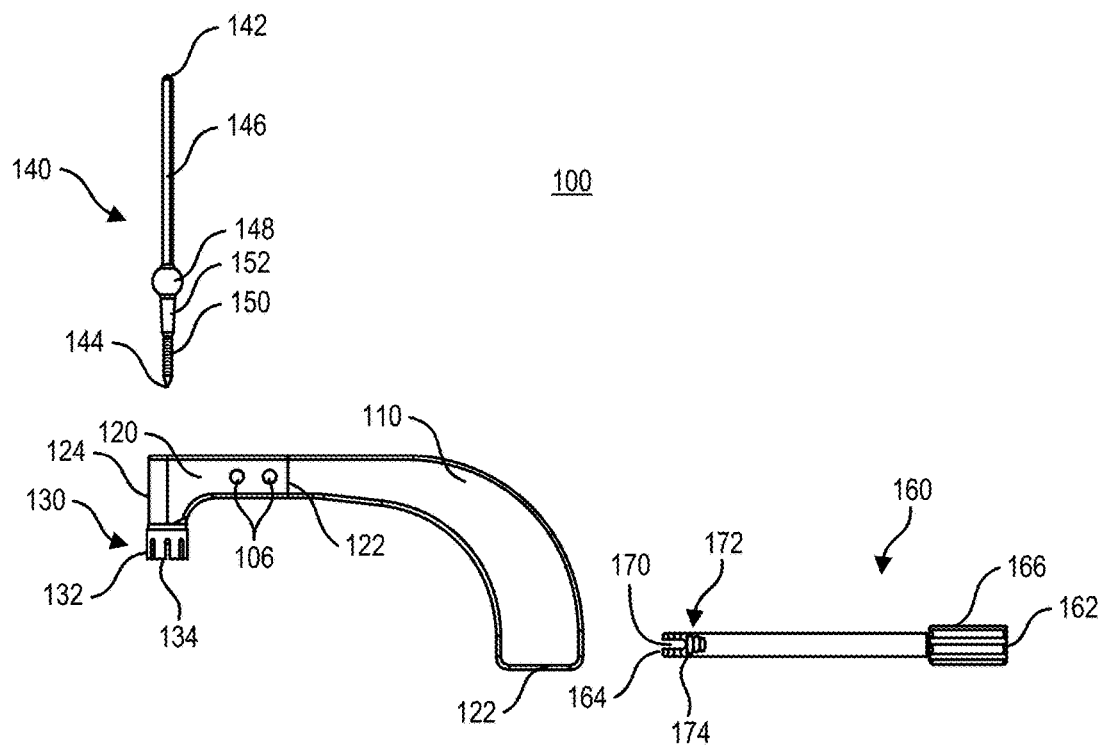
FIG. 6 is an exploded, top view of the implant alignment guide system of FIG. 3, in accordance with an aspect of the present invention.
Figure 7:
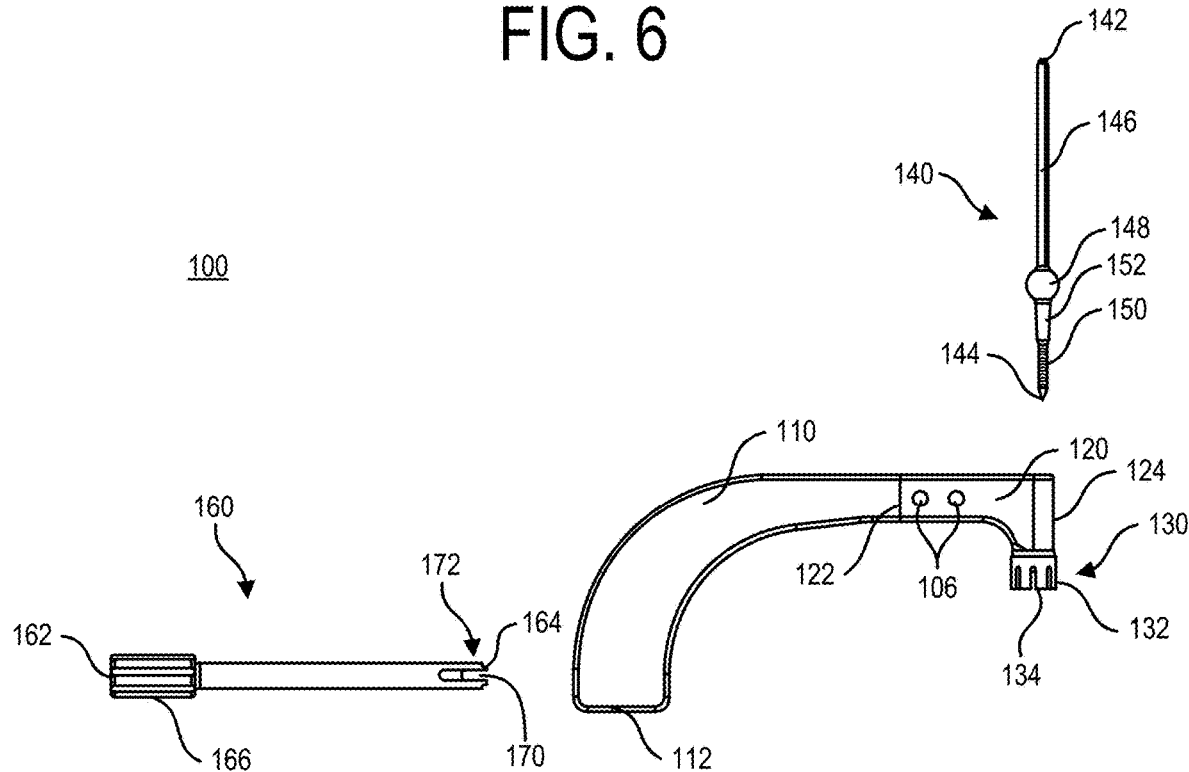
FIG. 7 is an exploded, bottom view of the implant alignment guide system of FIG. 3, in accordance with an aspect of the present invention.

As shown in FIGS. 4-7, the guide sleeve insert 160 may have a first end 162 and a second end 164. The guide sleeve insert 160 may have a handle portion 166 at the first end 162 and a shaft 168 extending from the handle portion 166 to the second end 164. The second end 164 may include a channel 170 extending into the shaft 168. As shown in FIG. 6, the second end 164 may also include a contact portion 172 for contacting a patient's foot, as shown in FIGS. 2, 3 and 6. The contact portion 172 may include, for example, a plurality of protrusions or other textured surface 174 to assist with contacting the patient's foot. The guide sleeve insert 160 may be, for example, cannulated to allow for insertion of the guide wire 180. The guide wire 180 may have a first end 182 and a second end 184. The second end 184 of the guide wire 180 may have a pointed or sharp tip for insertion into a patient's bone.

Referring now to FIGS. 11-22, a fixation guide 200 is shown. The fixation guide 200 includes an outrigger assembly or frame 210 which may be coupled to a compression device 260 and an intramedullary nail 300. The frame 210 may include a first end 202 and a second end 204. The frame 210 may include at least one opening 206 allowing for visualization through the frame 210 with imaging technology, such as x-rays, as seen in FIGS. 15-18. The frame 210 is ideally made of a material that is strong enough to prevent deformation during surgery, for example, a metal, such as aluminum, a composite, such as carbon fiber, or the like. The frame 210 may also be radiolucent to allow for imaging through the frame 210 for determining if correct alignment of the nail 300 was achieved.

In the embodiment depicted in FIGS. 19-22, the outrigger assembly 210 includes a base portion 212 and a guide portion 240. The base portion 212 includes first or lateral arm 214 and a second or distal arm 218. The lateral arm 214 extends generally perpendicular to the top surface of the base portion 212 and angled in a proximal-distal direction. The lateral arm 214 includes a first drill hole 216 extending through the arm 214 in a medial-lateral direction. The distal arm 218 extends generally perpendicular to the base portion 212 at the distal end and includes a knob opening or first opening 220, a nail attachment opening or second opening 222, and a nail attachment portion or apparatus 224. The nail attachment portion 224 includes an end with an inverted two step profile including a first step or first nail attachment segment 226 extending a first distance and a second step or second nail attachment segment 228 extending a second distance. The first distance is greater than the second distance.

Figure 20:
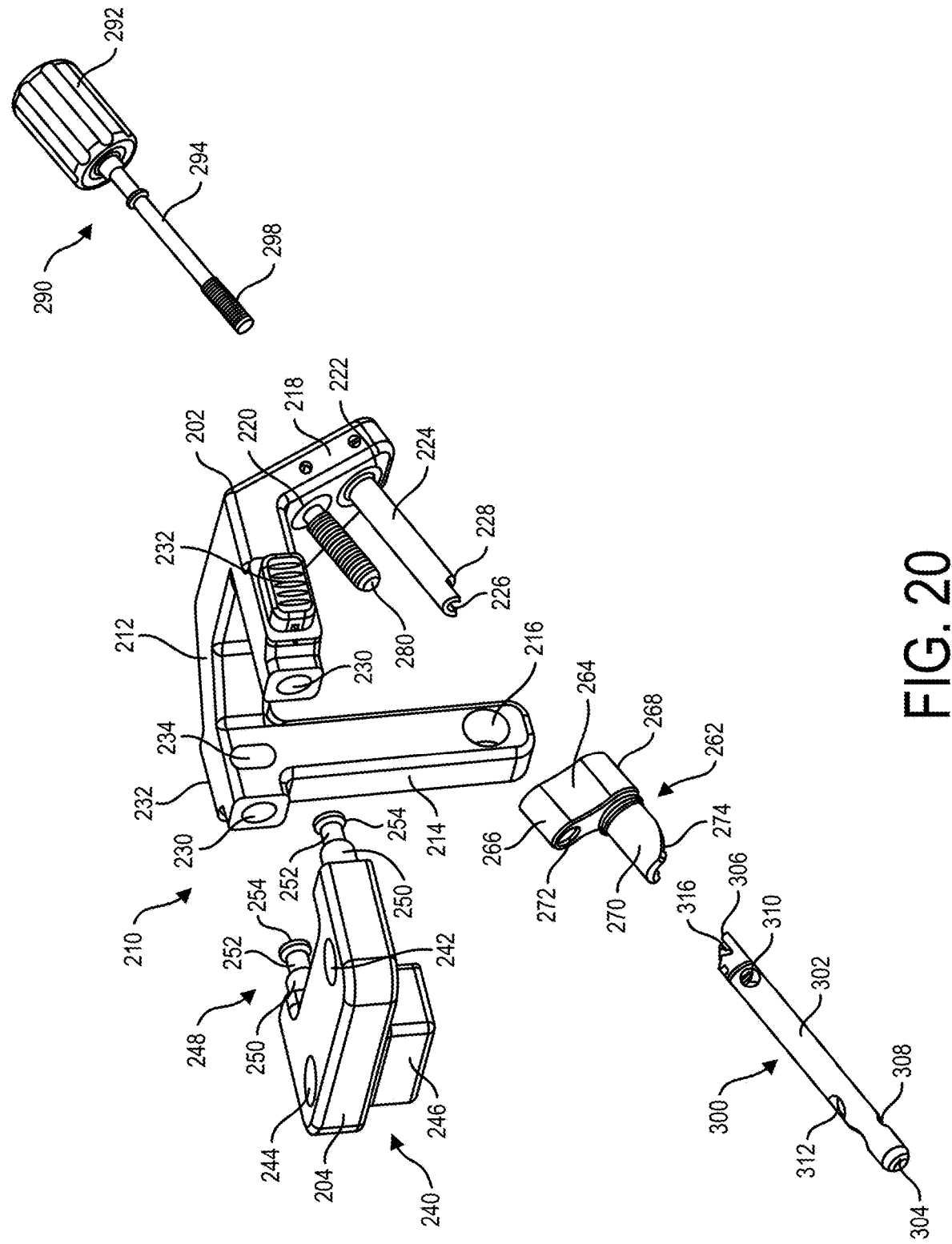
FIG. 20 shows a perspective view of the fixation guide of FIG. 12, in accordance with an aspect of the present invention.
Figure 22:
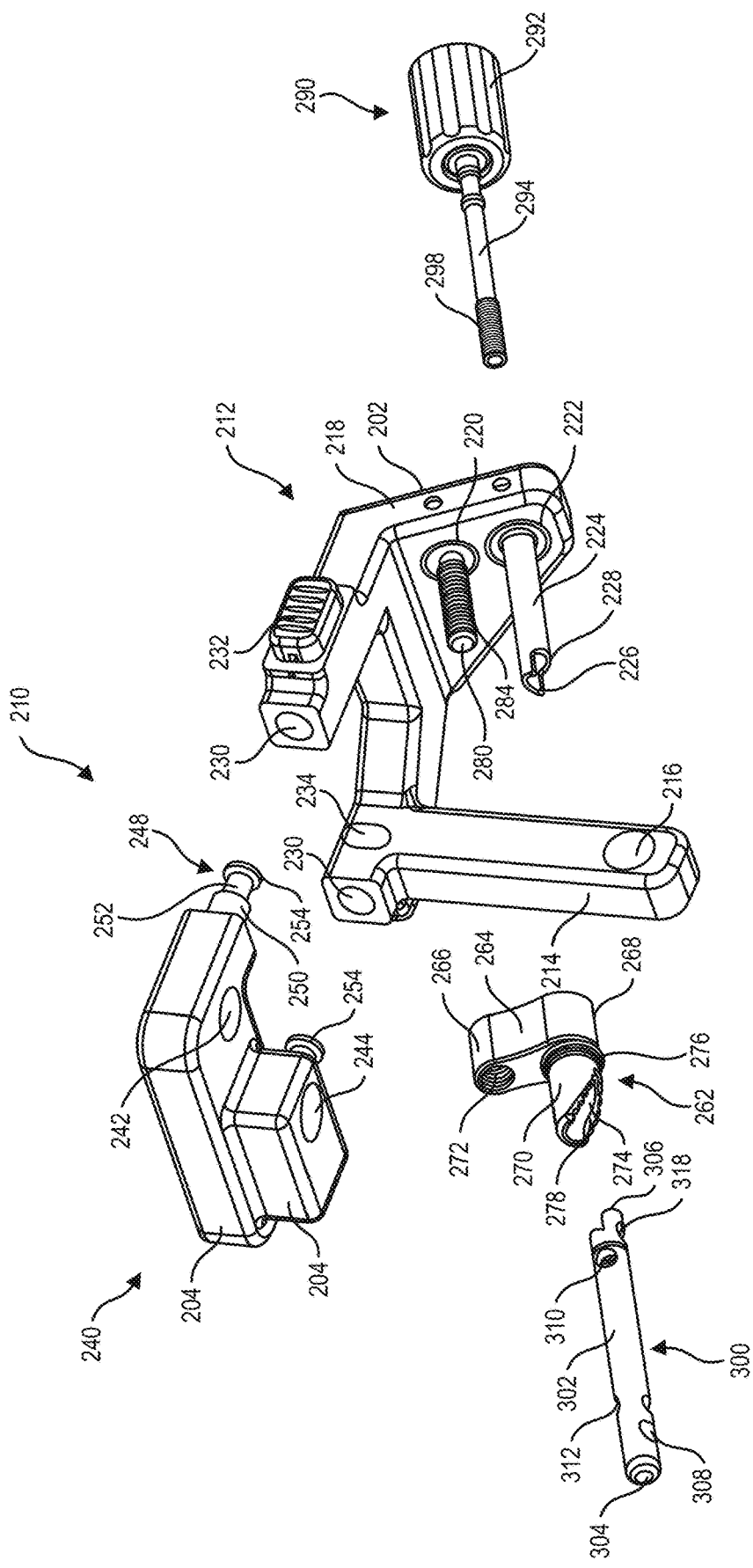
FIG. 22 is an exploded, second end perspective view of the fixation guide of FIG. 12, in accordance with an aspect of the present invention.

As shown in FIGS. 20 and 22, the base portion 212 may also include two locking openings 230 for coupling the base portion 212 to the guide portion 240. The locking openings 230 extend into the base portion 212 from a proximal end. In addition, the base portion 212 may include two buttons or release buttons 232. The release buttons 232 may include a portion that extends into the locking openings 230 to couple to the guide portion 240. When depressed the release buttons 232 disengage from the guide portion 240 and allow for removal of the guide portion 240 from the base portion 212.

The guide portion 240 includes a second drill hole 242 and a third drill hole 244, as shown in FIGS. 12, 15-18, and 20-22. The second and third drill holes 242, 244 may each be positioned at different angles relative to the top surface of the guide portion 240. The third drill hole 244 may extend from the top surface of the guide portion 240 through a projection 246 extending away from a bottom surface of the guide portion 240. The guide portion 240 may also include two arms 248 for engaging the two locking openings 230 of the base portion 212. The arms 248 may include a base 250 coupled to the guide portion 240, a recessed region 252 extending away from the base 250, and a locking projection 254 extending away from the recessed region 252. The locking projections 254 having a diameter or size larger than a diameter or size of the recessed region 252. Multiple guide portions 240 may be provided to engage the base portion 212 and each guide portion 240 may include openings 242, 244 that correspond to the position of the openings 308, 312 in different size intramedullary nails 300. Alternatively, it is also contemplated that the guide portion 240 may include, for example, a plurality of drill holes 242, 244 as necessary to secure the intramedullary nail 300 across a joint or fracture. The drill holes 242, 244 may each include, for example, multiple holes spaced a small distance apart or multiple nested or overlapping holes to correspond to the openings 242, 244 in multiple size intramedullary nails 300.

Figure 21:
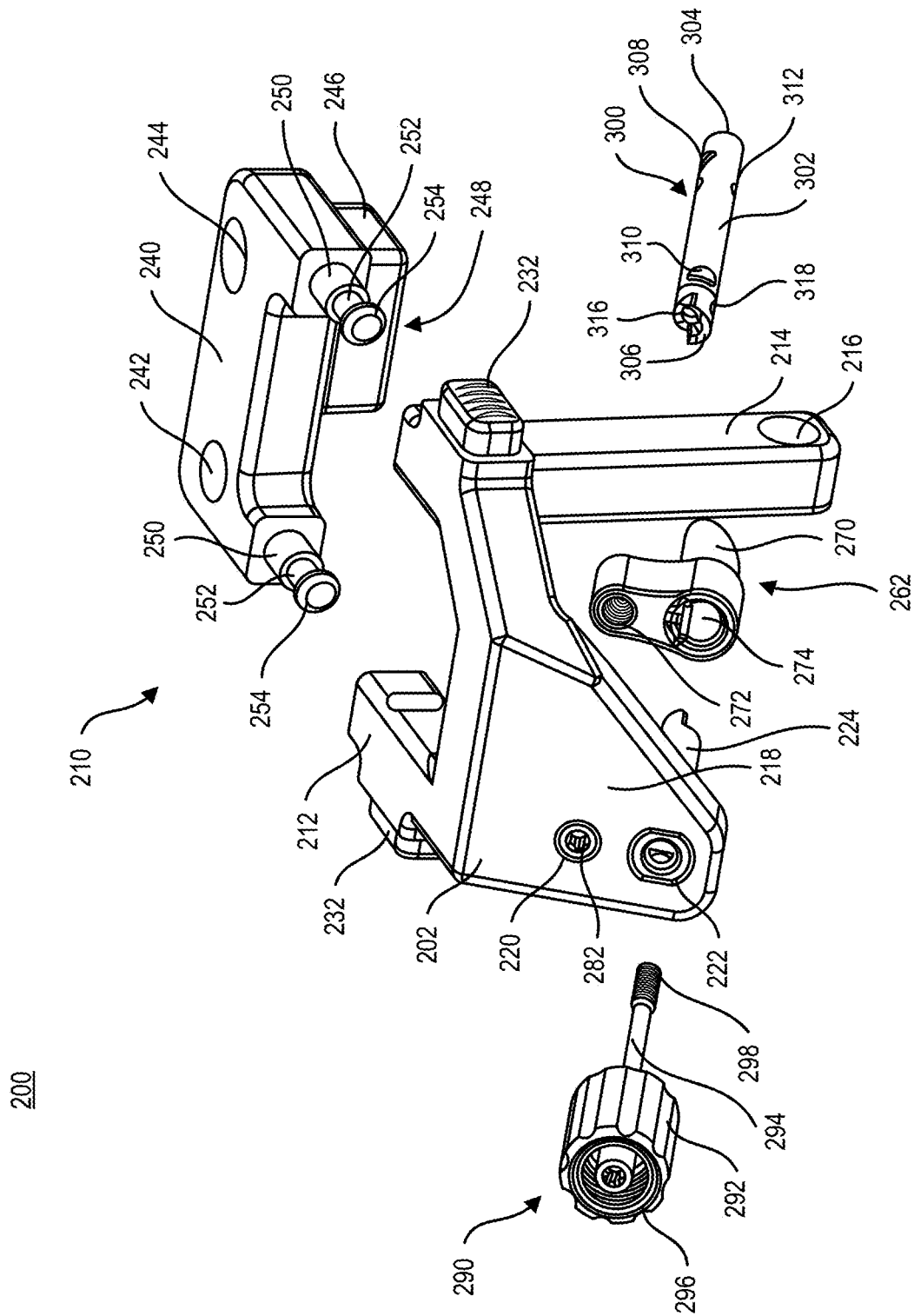
FIG. 21 is an exploded, first end perspective view of the fixation guide of FIG. 12, in accordance with an aspect of the present invention.

When the arms 248 are inserted into the locking openings 230 of the base portion 212, the arms 248 may extend past the release buttons 232. The release buttons 232 may include, for example, an extension member 234 extending through and perpendicular to the locking openings 230, as shown in FIGS. 21 and 22. The extension members 234 may include, for example, an opening (not shown) that may be aligned with the locking openings 230 in the base portion 212. For example, when the release buttons 232 are depressed, the openings (not shown) in the extension members 234 may be directly aligned with the locking openings 230 to allow for the arms 248 to be inserted through the openings in the extension members 234. During insertion, once the locking projections 254 pass through the openings (not shown) in the release buttons 232, the buttons 232 may be released and the extension members 234 may engage the recessed regions 252 to secure the guide portion 240 to the base portion 212. During removal of the guide portion 240, the release buttons 232 may be depressed to align the openings in the extension members 234 with the locking openings 230. Next, the guide portion 240 may be removed from the base portion 212 by pulling the guide portion 240 until the locking projections 254 pass through the openings (not shown) in the extension members 234 and out of the locking openings 230.

Figure 12:
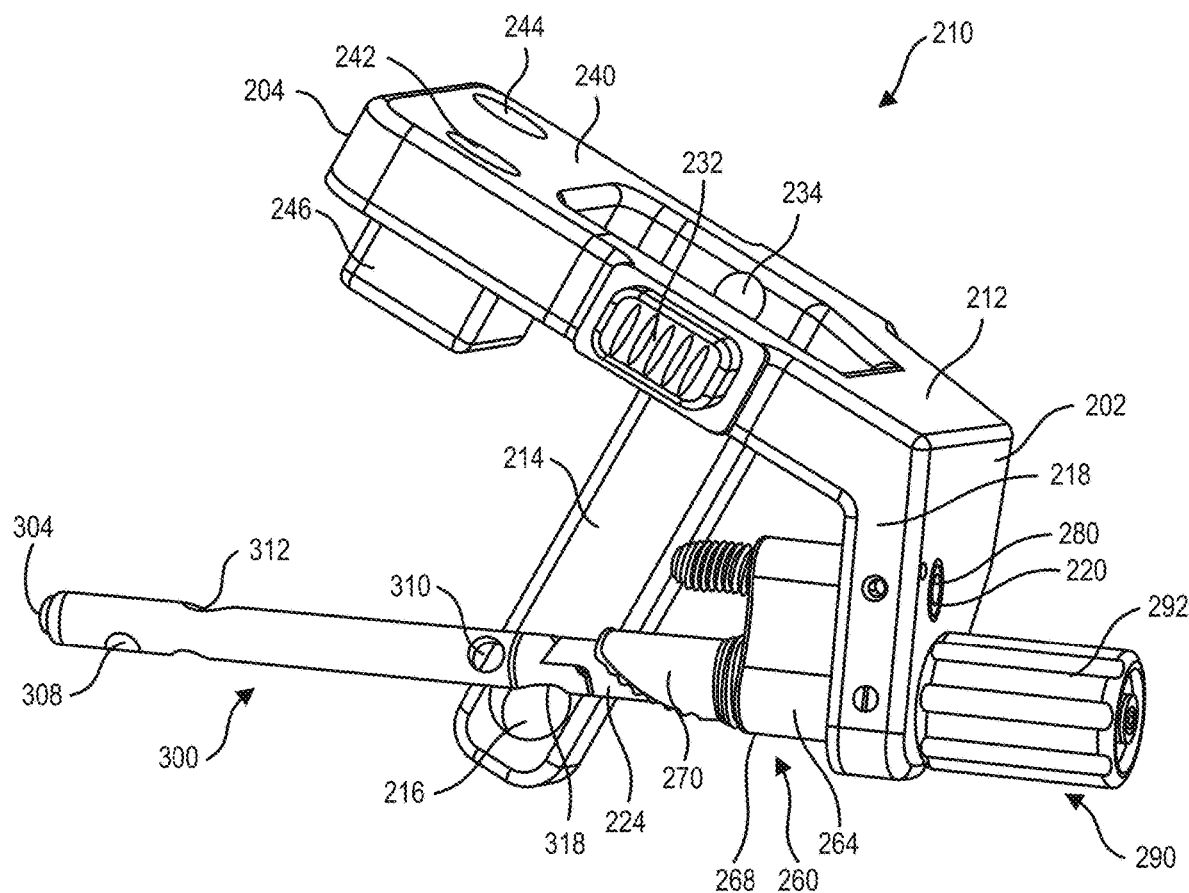
FIG. 12 is a side perspective view of the fixation guide of FIG. 11, in accordance with an aspect of the present invention.
Figure 13:
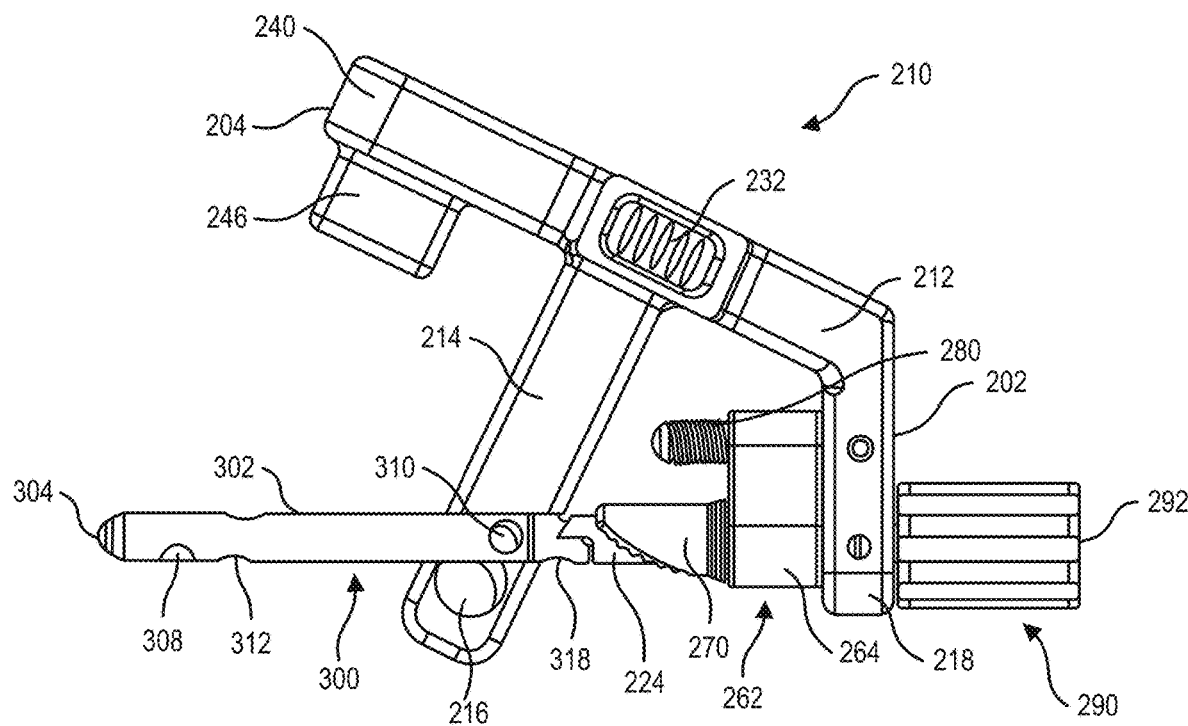
FIG. 13 is a medial view of the fixation guide of FIG. 12, in accordance with an aspect of the present invention.
Figure 14:
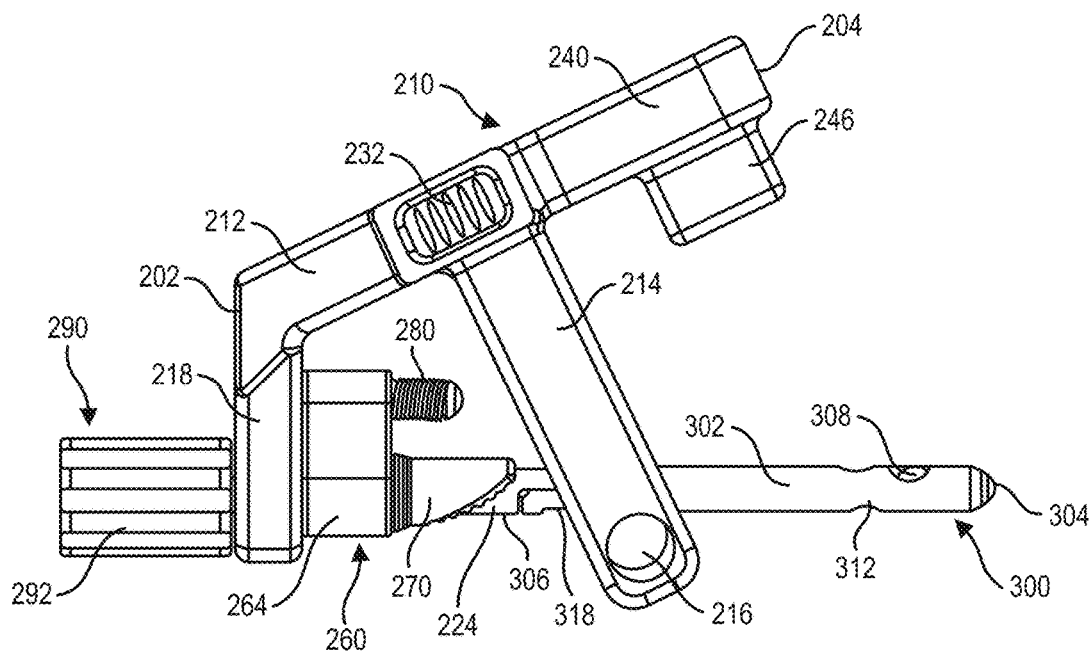
FIG. 14 is a lateral view of the fixation guide of FIG. 12, in accordance with an aspect of the present invention.
Figure 16:
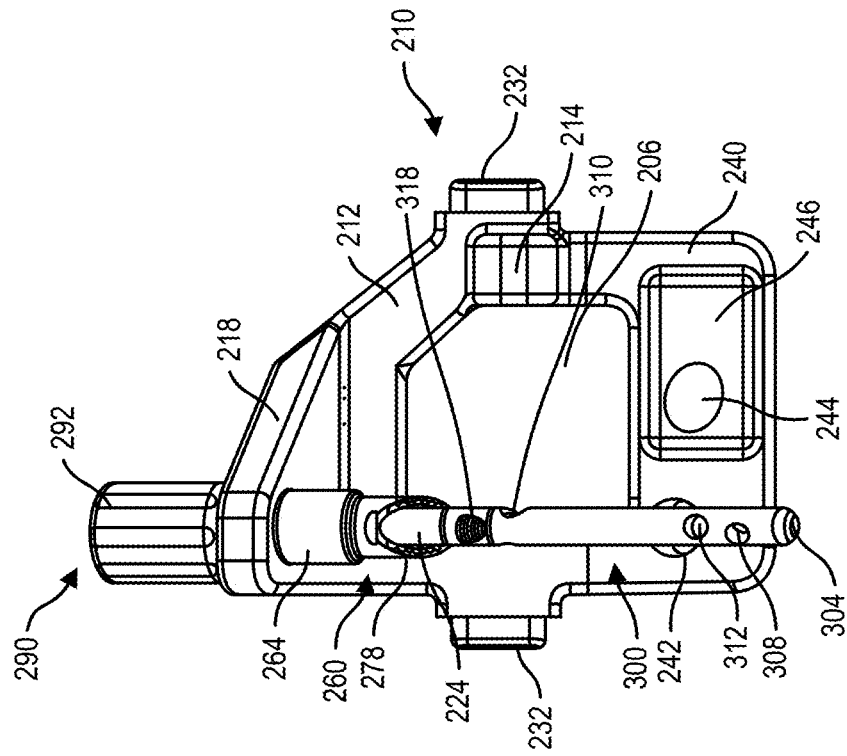
FIG. 16 is a bottom view of the fixation guide of FIG. 12, in accordance with an aspect of the present invention.
Figure 15:
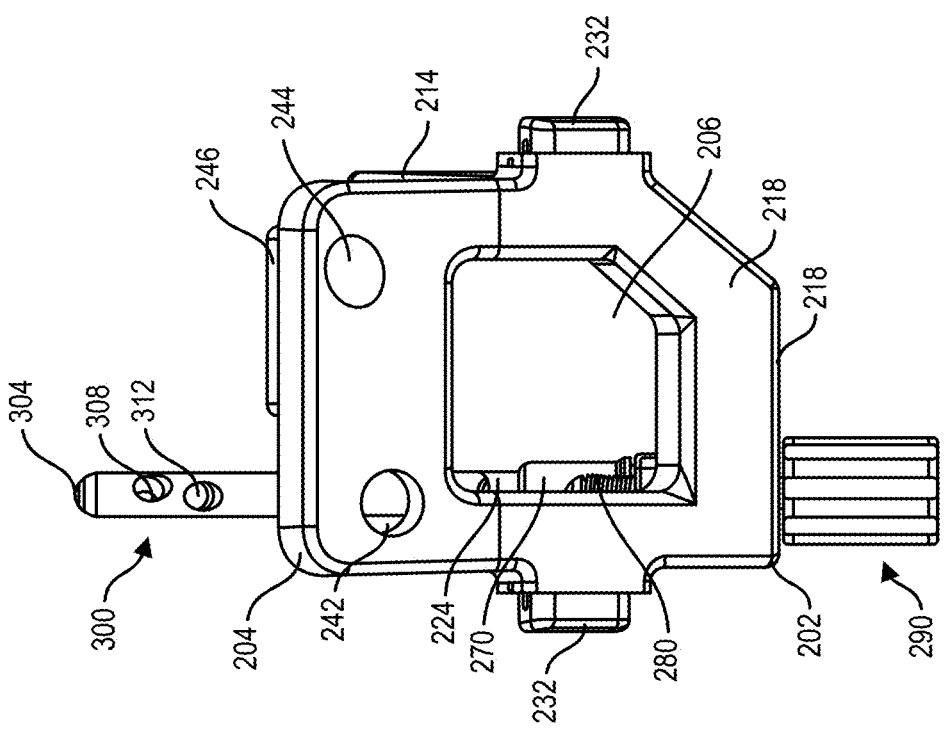
FIG. 15 is a top view of the fixation guide of FIG. 12, in accordance with an aspect of the present invention.
Figures 17, 18:
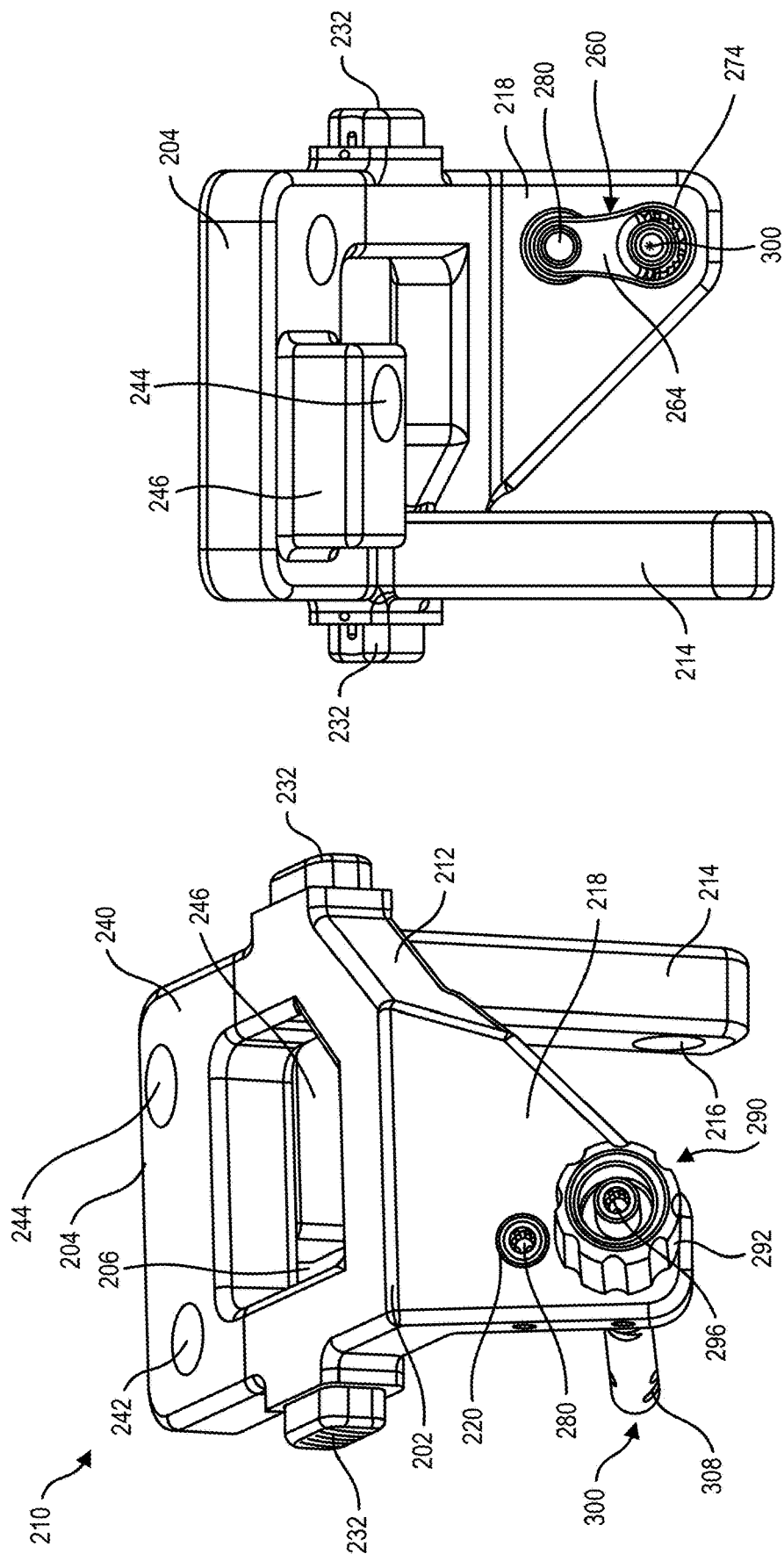
FIG. 17 is a first end view of the fixation guide of FIG. 12, in accordance with an aspect of the present invention.
FIG. 18 is a second end view of the fixation guide of FIG. 12, in accordance with an aspect of the present invention.

The compression device 260 slidingly mates with the nail attachment portion 224, as shown in FIGS. 12-14. The compression device 260 includes a compression member 262, a bolt 280, and an engagement fastener 290. As best seen in FIGS. 21 and 22, the compression member 262 has a base 264 with a top end 266 and a bottom end 268. The compression member 262 also includes a protrusion 270 at the bottom end 268. A first opening 272 is near the top end 266 for receiving bolt 280. The first opening 272 is threaded to mate with a threaded end 284 of bolt 280. A second opening 274 is near the bottom end 268 and passes through the base 264 and protrusion 270. The second opening 274 is slidingly engaged with the nail attachment portion 224. The proximal end of the compression member 262 is angled from a point between the top and midline of the protrusion 270 to approximately a midpoint 276 of the bottom end 268 of the base 264 of the compression member 262. The angled portion of the protrusion 270 may include teeth or a texture surface 278 for engaging a patient's bone. The angled portion may have an angle that, for example, mimics or corresponds to the angle of the bone it contacts.

As depicted, after the compression member 262 is slid over nail attachment portion 224, the compression member 262 may be secured to the base 212 using the bolt 280, as shown in FIGS. 12-18. The threaded end 284 of bolt 280 is inserted into first opening 220 and the threaded end 284 mates with the threads of the first opening 272. The bolt 280 may also include a stop member (not shown). The stop member (not shown) prevents bolt 280 from passing through first opening 220. The bolt 280 may also include a drive opening in the head portion 282 for rotating the bolt 280 to engage and disengage from the compression member 262. Alternatively, a torque indicating or limiting driver (not shown) including, for example, a torque meter may be used to turn the bolt 280.

An alternative compression member 262 is also contemplated. The alternative compression member 262 may include a force gauge (not shown) to directly measure the compressive force. The force gauge (not shown) may include gauge indicators or markings (not shown) positioned along the longitudinal axis of the base 264 to show the compressive force being applied.

As shown in FIGS. 21 and 22, the engagement fastener 290 includes a knob 292 coupled to a shaft 294. The shaft 294 includes a drive opening 296 at a first end and a threaded portion 298 at a second end. Although the threaded portion 298 is shown as only including threads on a portion of the shaft 294, it is also contemplated that the shaft 294 could be threaded along its entire length. The drive opening 296 may be, for example, hexagonal, square, Phillips or another multi-lobed configuration for coupling with an insertion instrument. The shaft 294 is inserted through the nail attachment opening 222 and the threaded end 298 couples to the intramedullary nail 300 to secure the fixation guide 200 to the nail 300.

Referring now to FIGS. 11-17 and 19-22, the intramedullary nail 300 includes a body 302 with a closed end 304, a fastening end 306, and openings 308, 310, 312. The openings 308, 310, 312 may be, for example, three openings disposed on independent planes and angularly spaced apart relative to each other. By placing the three openings 308, 310, 312 at opposing angles oblique to the longitudinal axis of the nail 300, the amount of longitudinal and rotational movement of the nail 300 is limited. It is also contemplated that the intramedullary nail 300 may include any number of openings 308, 310, 312 as may be necessary to secure the nail 300 to a patient's bones. The fastening end 306 includes an insertion opening 316 and an engagement opening 318. The insertion opening 316 is a threaded opening along a longitudinal axis in the center of the nail 300 parallel to the exterior surface of the nail 300. The insertion opening 316 is used to secure the nail 300 to the nail attachment portion 224 using an engagement fastener 290, such as a thumb screw. The engagement opening 318 may include a central axis that is generally transverse the longitudinal axis of the nail 300. The engagement fastener 290 is inserted through opening 222 and passes through the nail attachment portion 224 before being screwed into the insertion opening 316 to secure nail 300 to the nail attachment portion 224.

Figure 11:
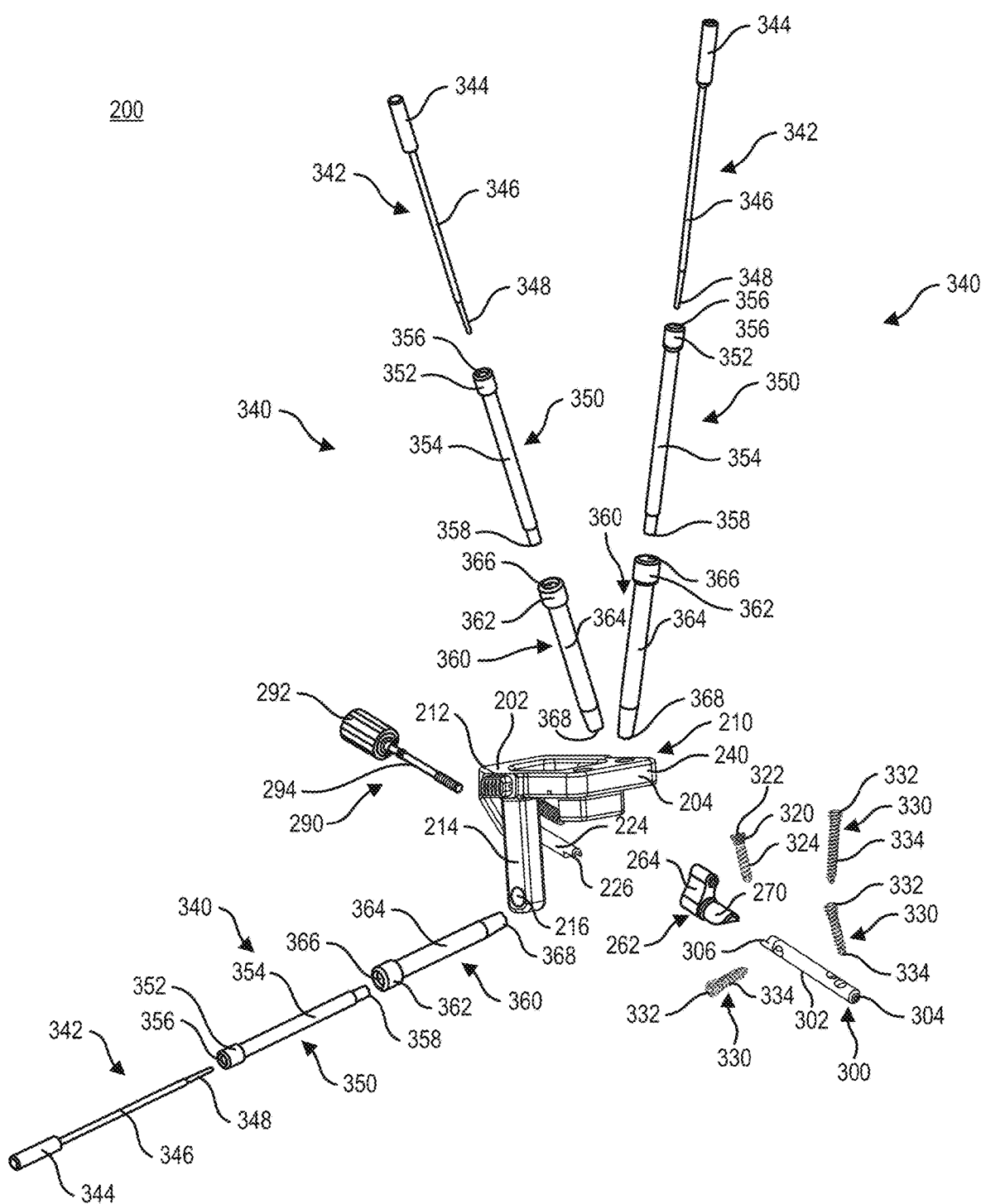
FIG. 11 is an exploded, side perspective view of a fixation guide system, in accordance with an aspect of the present invention.

The engagement opening 318 of the nail 300 may be a threaded opening that passes through the exterior surface of nail 300 to secure the nail 300 to the bone using a fastener, such as a locking screw 320. The locking screw 320 is depicted in FIG. 11 and includes a head 322 with a drive opening (not shown) and a threaded shank 324. The drive opening (not shown) may be, for example, a Phillips opening, a flat head opening, a hexagonal opening, or other multi-lobed configuration. The threaded shank 324 is designed to engage the patient's bone at the distal end and the threads (not shown) in the engagement opening 318 to secure the nail 300 in place inside the patient's bones.

Figure 19:
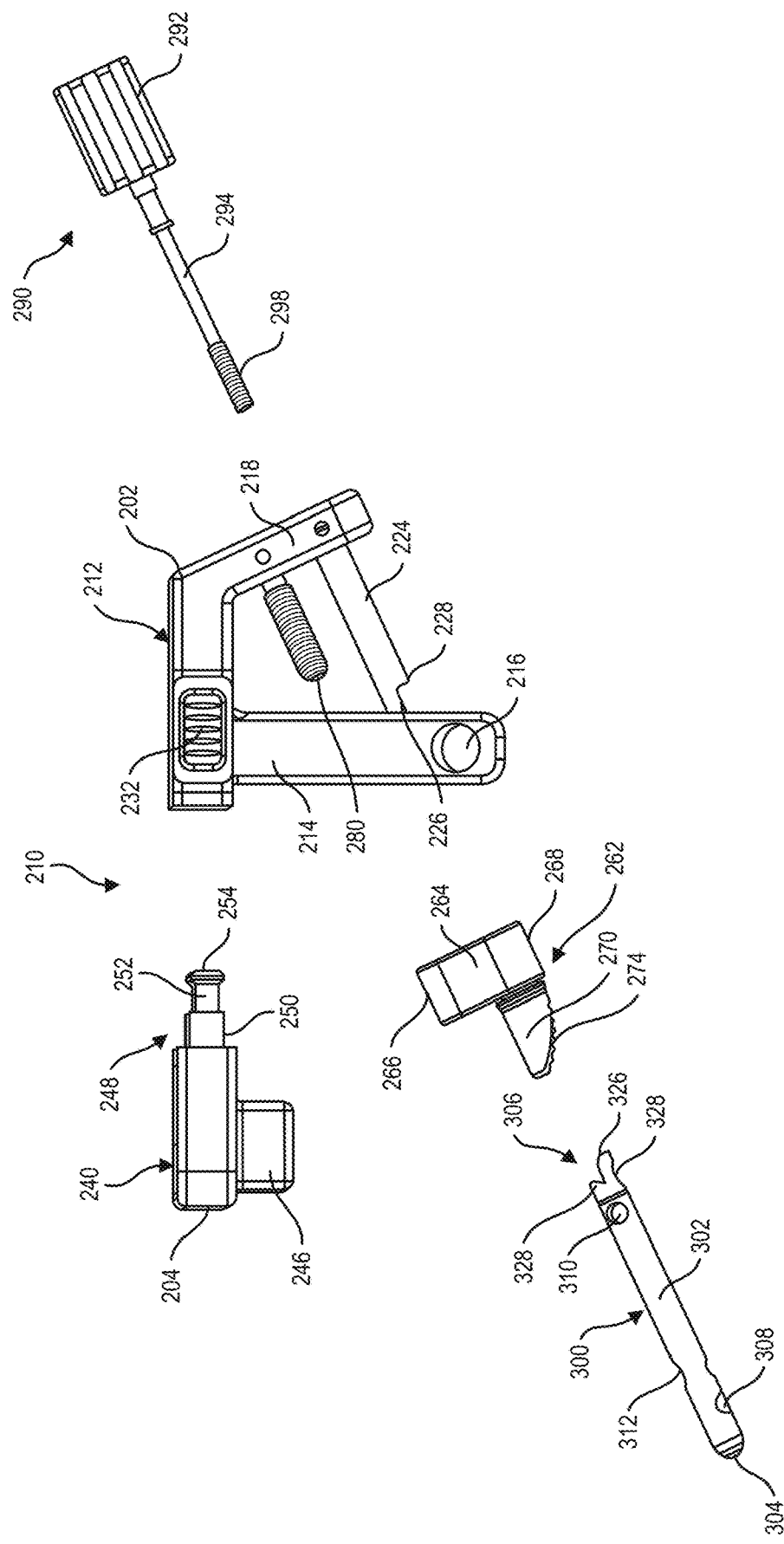
FIG. 19 is an exploded, side view of the fixation guide of FIG. 12, in accordance with an aspect of the present invention.

The nail 300 may also include a fastening end 306 with a shape that corresponds to the shape of the end of the nail attachment portion 224 to create a tight fit between the nail 300 and the attachment portion 224. As depicted in FIG. 19, the fastening end 306 may have a two-step profile including a first step or first fastening segment 326 and a second step or second fastening segment 328. When the nail 300 is secured to the outrigger assembly 210 the first fastening segment 326 aligns with second nail attachment segment 228 and second fastening segment 328 aligns with first nail attachment segment 226. The engagement fastener 290 may then be inserted to secure the nail 300 to the outrigger assembly 210. The step profiles of the nail 300 and the nail attachment portion 224 provide additional stability to the nail 300 during insertion into the patient's bone and prevent nail 300 from rotating during insertion of the pegs and screws.

The fixation guide 200 may be used with at least one guide system 340, as shown in FIG. 11. The guide system 340 may be used for insertion of pegs or locking screws 330 through the intramedullary nail 300. The pegs 330 may include a head portion 332 with a drive opening (not shown) and a threaded shaft 334. The guide system 340 may include an obturator 342, drill guide 350, and a screw guide 360. The guide system 340 may also include a pin guide 370, as shown in FIG. 33. The obturator 342 may include a handle portion 344 coupled to a first end of a shaft portion 346 and a tip 348 at the second end of the shaft portion 346. The drill guide 350 may include a grip portion 352 at a first end of a shaft portion 354. The drill guide 350 may also include a cannulation 356 extending from the first end to the second end of the shaft portion 354. The cannulation 356 may be, for example, sized to receive the obturator 342. In addition, the drill guide 350 may include teeth 358 at the second end for engagement with the patient's bones. The screw guide 360 may include a grip portion 362 at a first end of the shaft portion 364. The screw guide 360 may also include a cannulation 366 extending from the first end to the second end of the shaft portion 364. The cannulation 366 may be, for example, sized to receive the drill guide 350. In addition, the screw guide 360 may include teeth 368 at the second end for engagement with the patient's bone.

The fixation guide 200 may also include a locking guide 380, as shown in FIG. 11. The locking guide 380 may be used for insertion of a locking screw 320 into the intramedullary nail 300. The locking guide 380 may include a grip portion 382 at a first end of a shaft portion 384. The locking guide 380 may also include a cannulation 386 extending from the first end to the second end of the shaft portion 384. The cannulation 386 may be, for example, sized to receive a drill bit or k-wire drill (not shown) for drilling an opening in the bone for insertion of the locking screw 320. The k-wire drill (not shown) may be used for both drilling the opening in the bone and as a pin for temporary fixation. In addition, the locking guide 380 may include threads 388 at the second end for engagement with the end of the intramedullary nail 300.

Figure 23:
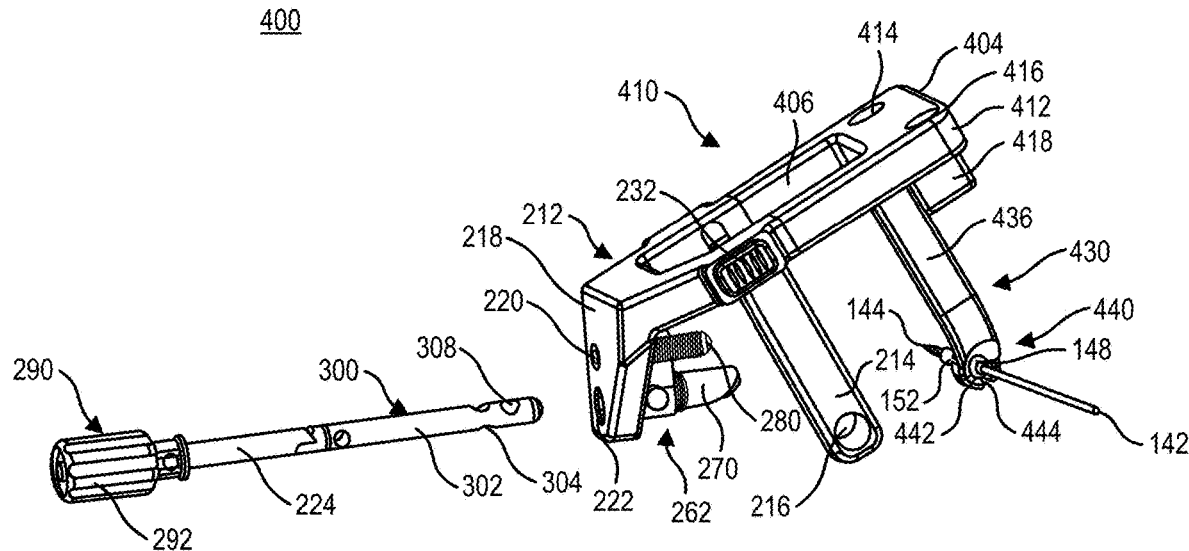
FIG. 23 is a partially exploded, lateral view of another embodiment of a fixation guide, in accordance with an aspect of the present invention.
Figure 24:
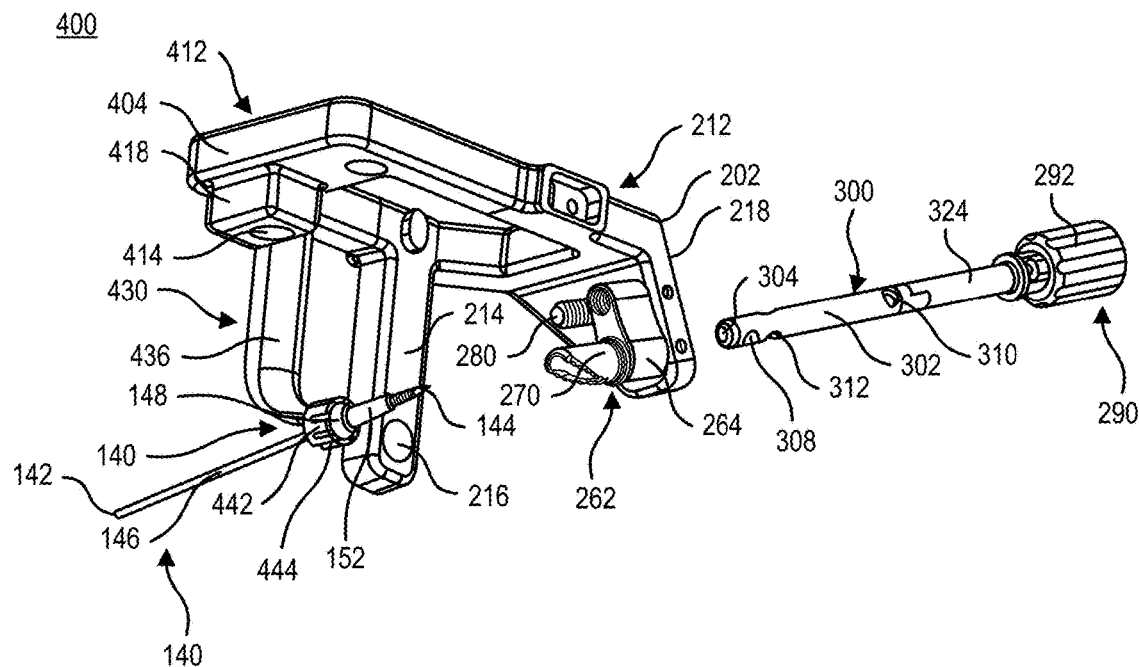
FIG. 24 is a partially exploded, medial view of the fixation guide of FIG. 23, in accordance with an aspect of the present invention.
Figure 25:
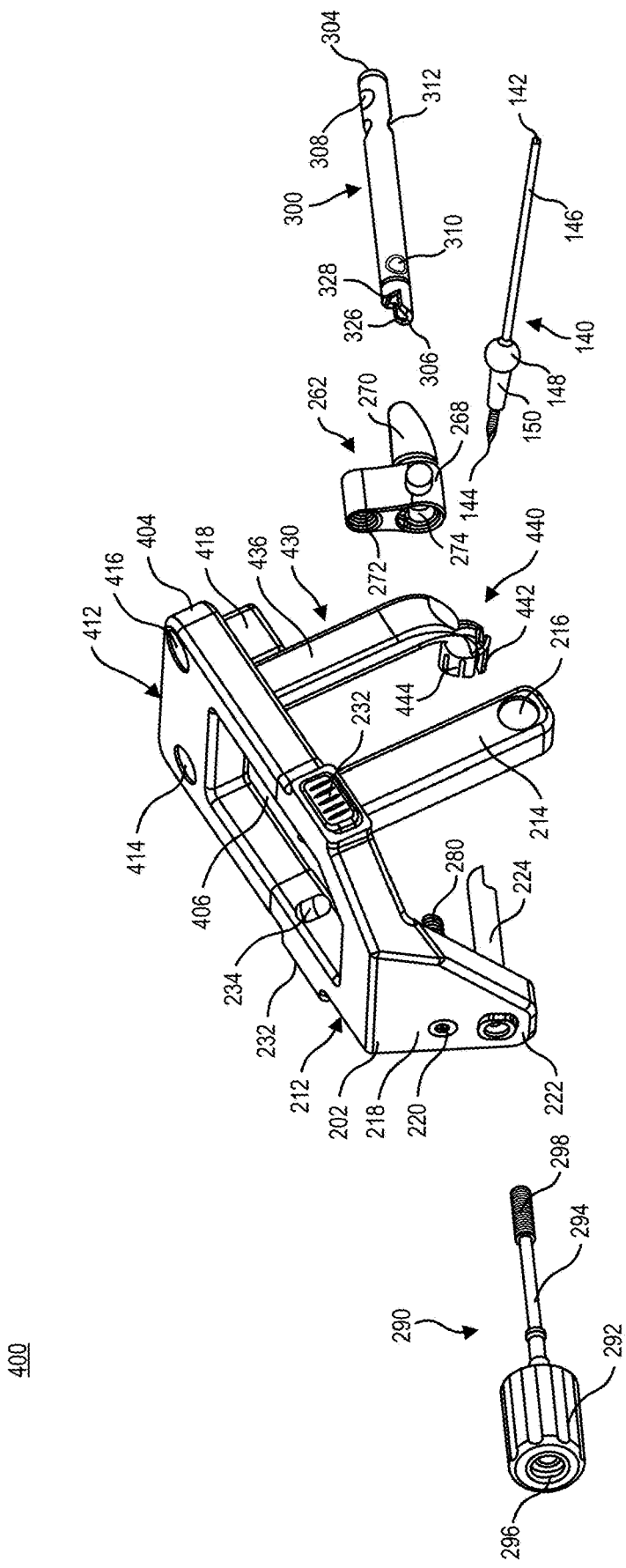
FIG. 25 is an exploded, lateral view of the fixation guide of FIG. 23, in accordance with an aspect of the present invention.

Another embodiment of a fixation guide 400 is shown in FIGS. 23-28. The fixation guide 400 includes an outrigger assembly or frame 410 which may be coupled to a compression device 260 and an intramedullary nail 300. The frame 410 may include a first end 402 and a second end 404. The frame 410 may also include at least one opening 406 allowing for visualization through the frame 410 with imaging technology, such as x-rays, as seen in FIGS. 23-25. The frame 410 is ideally made of a material that is strong enough to prevent deformation during surgery, such as a metal, while also being radiolucent to allow for imaging through the frame 410 to determine if correct alignment of the nail 300 was achieved. The frame 410 may be made of, for example, carbon fiber.

Figure 28:
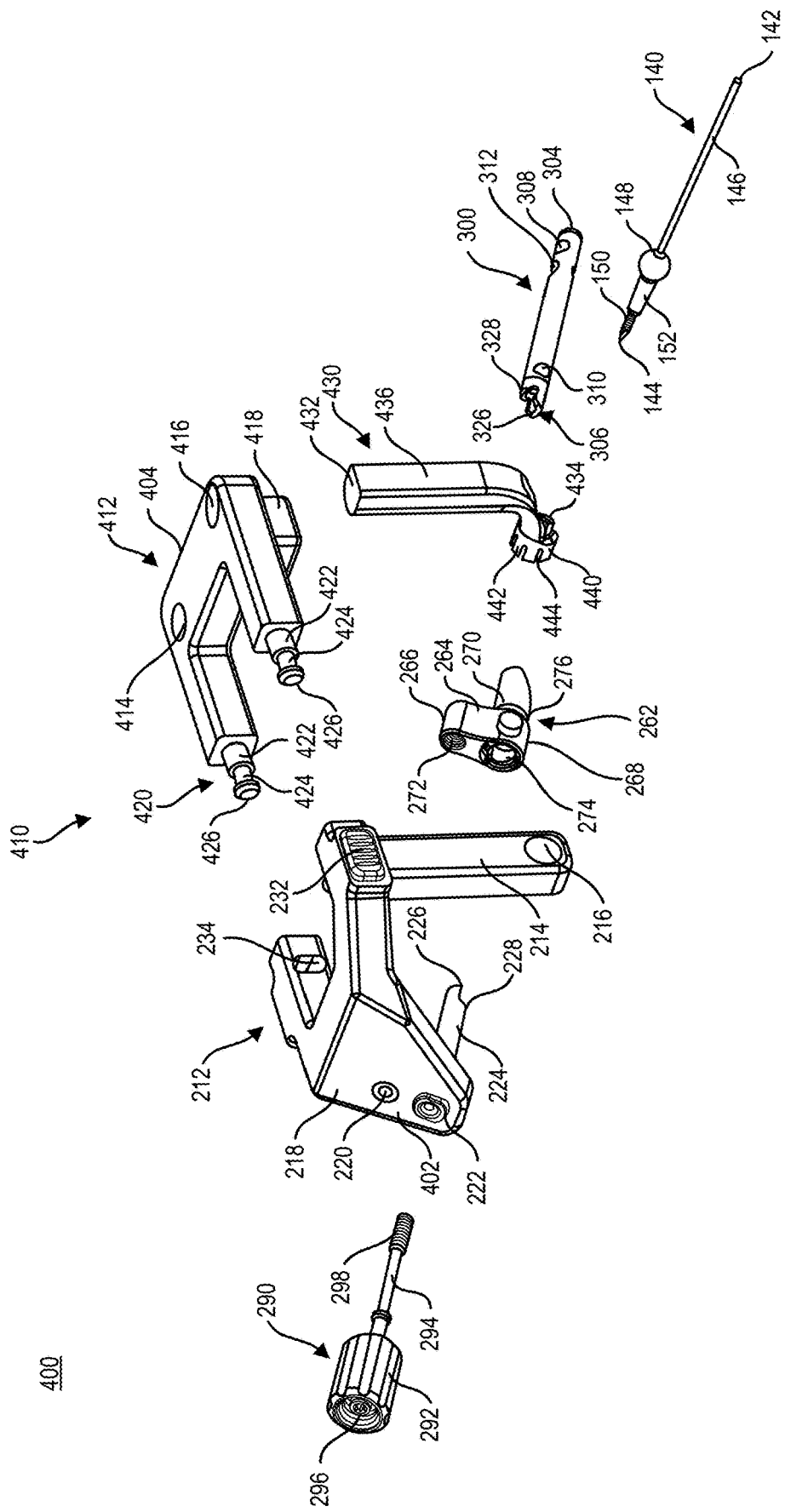
FIG. 28 is an exploded, perspective first side view of the fixation guide of FIG. 23, in accordance with an aspect of the present invention.
Figure 29:
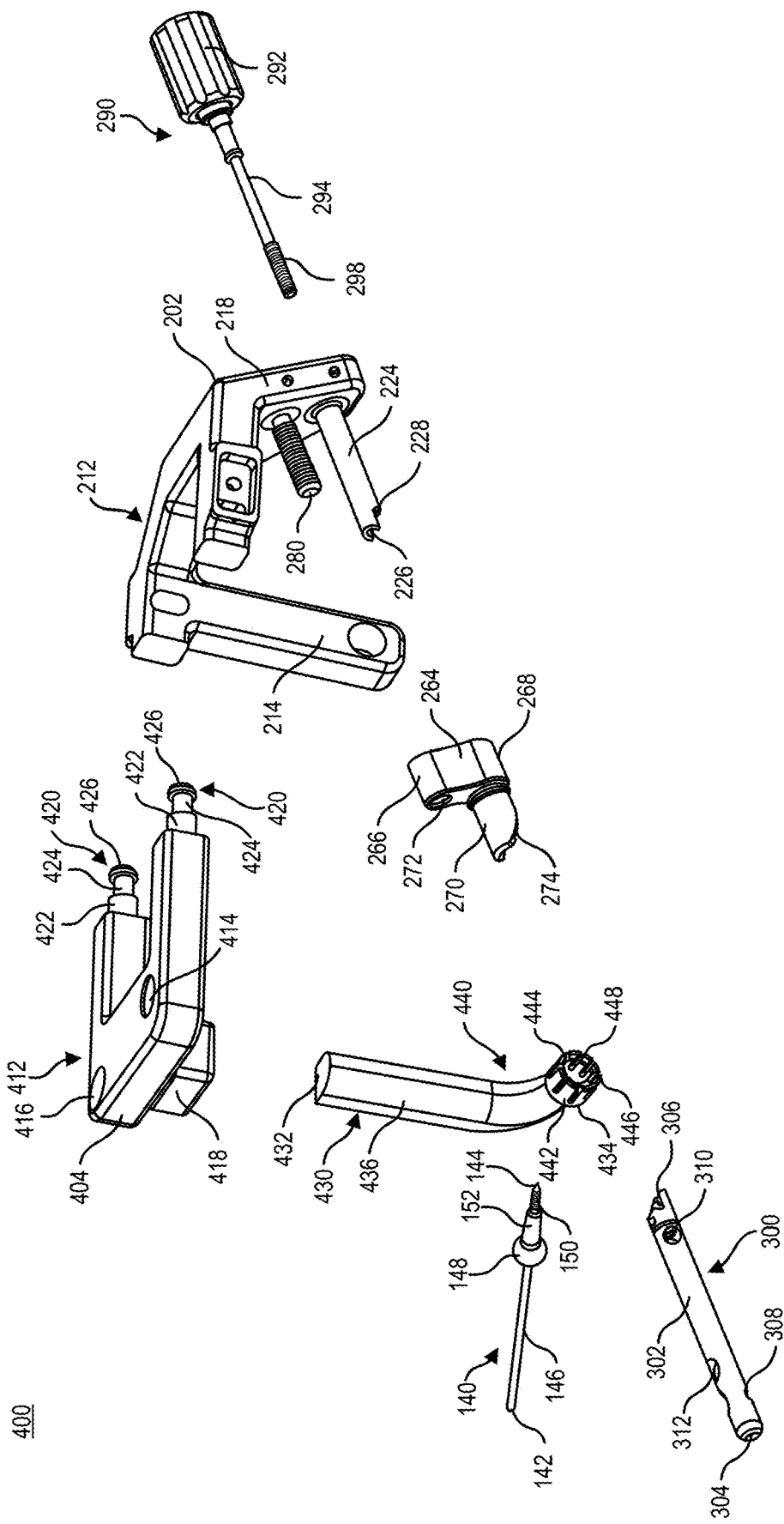
FIG. 29 is an exploded, perspective second side view of the fixation guide of FIG. 23, in accordance with an aspect of the present invention.

As shown in FIGS. 28-29, the frame 410 includes a base portion 212 and a guide portion 412. The base portion 212 may be as described above with reference to FIGS. 11-22, which will not be described again here for brevity sake. The guide portion 412 includes a second drill hole 414 and a third drill hole 416, as shown in FIGS. 23-26, 28 and 29. The second and third drill holes 414, 416 may each be positioned at different angles relative to the top surface of the guide portion 240. The third drill hole 244 may extend from the top surface of the guide portion 412 through a projection 418 extending away from a bottom surface of the guide portion 412. Multiple guide portions 412 may be provided to engage the base portion 212 and each guide portion 412 may include openings 414, 416 that correspond to the position of the openings 308, 312 in different size intramedullary nails 300. Alternatively, it is also contemplated that the guide portion 412 may include, for example, a plurality of drill holes 414, 416 as necessary to secure the intramedullary nail 300 across a joint or fracture. The drill holes 414, 416 may each include, for example, multiple holes spaced a small distance apart or multiple nested or overlapping holes to correspond to the openings 414, 416 in multiple size intramedullary nails 300.

Figure 26:
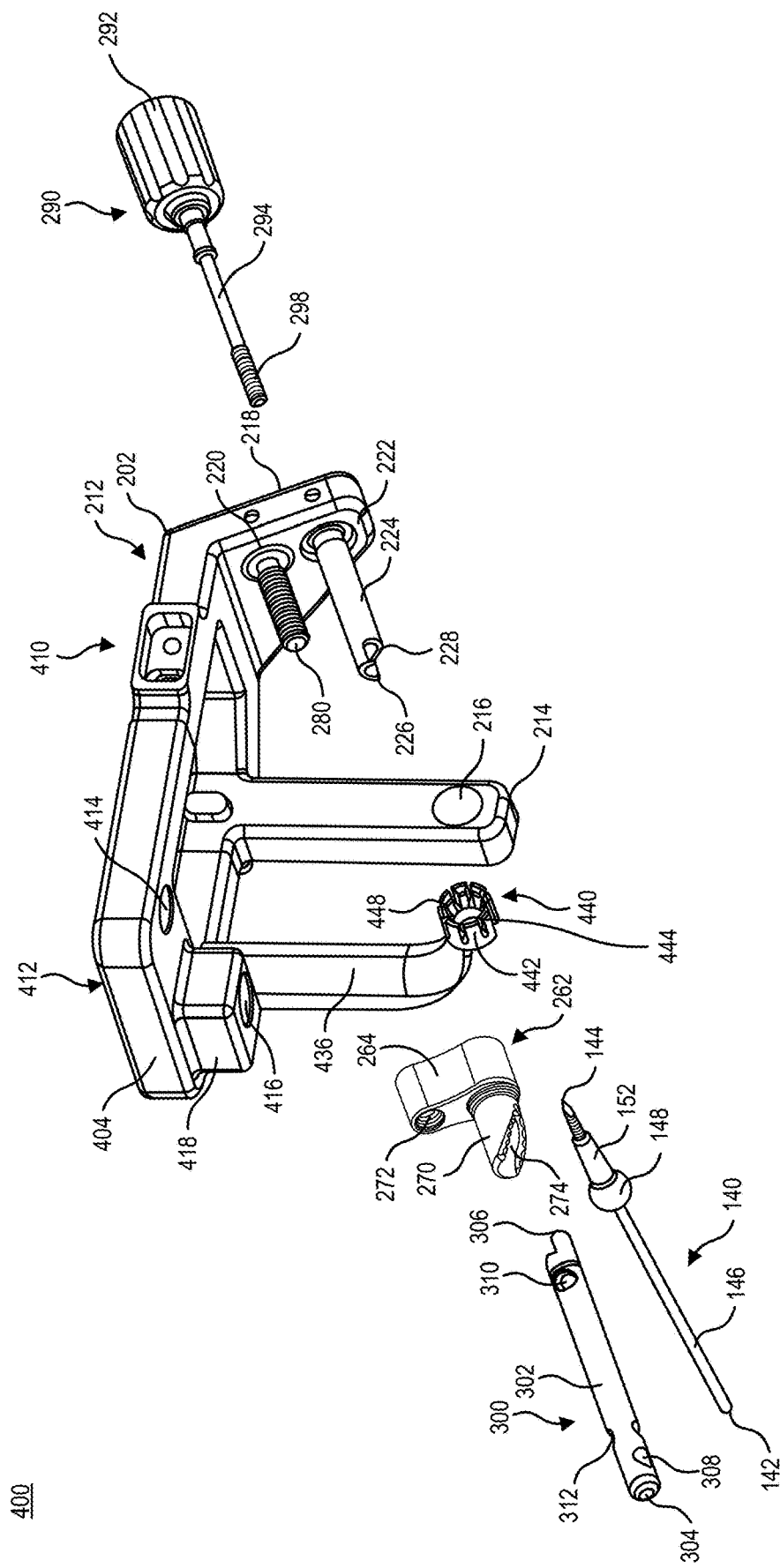
FIG. 26 is an exploded, medial view of the fixation guide of FIG. 23, in accordance with an aspect of the present invention.
Figure 27:
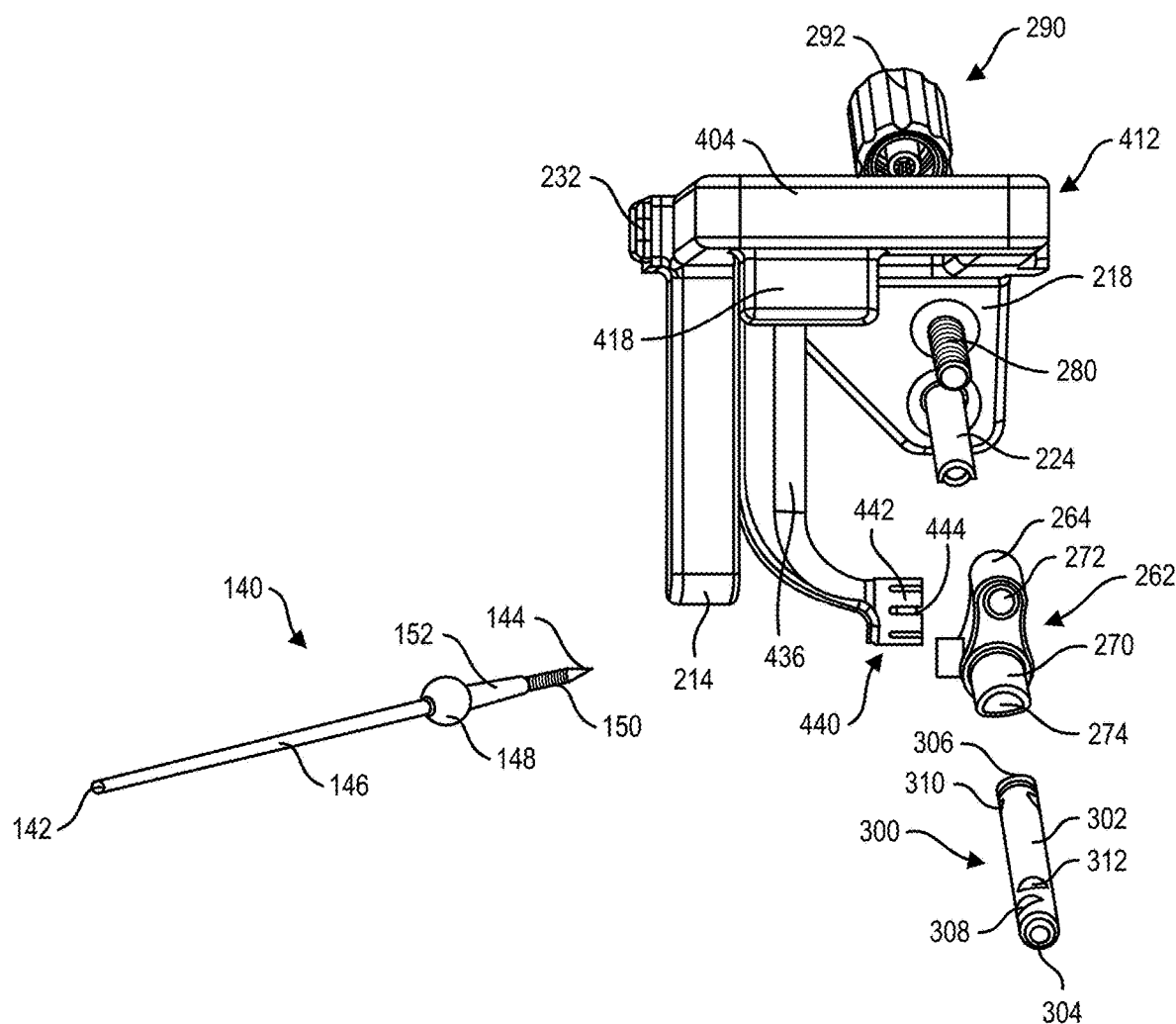
FIG. 27 is an exploded, end view of the fixation guide of FIG. 23, in accordance with an aspect of the present invention.

The guide portion 412 may also include an alignment arm 430, as shown in FIGS. 23-29. The alignment arm 430 has a first end 432 and a second end 434. The first end 432 may be coupled or secured to a bottom surface of the guide portion 412. The second end 434 may include a pivoting end 440 for receiving the pivoting member 140. The pivoting end 440 may include, for example, a plurality of teeth, protrusions, or extension members 442 alternating with a plurality of grooves or reliefs 444 around the circumference of the pivoting end 440. Each of the plurality of teeth 442 may be, for example, curved on the interior surface of the pivoting end 440 to form a curved region 446, as shown in FIGS. 26 and 29. The curved region 446 on each of the plurality of teeth 442 may form a spherical opening or opening with a circular or round cross-section on the interior surface of the pivoting end 440. The shape formed by the curved regions 446 may, for example, match the shape of the pivot protrusion 148 of the pivoting member 140. The plurality of teeth 442 may also include, for example, a projection or extension 448 positioned near the plantar end of the alignment arm 430 and extending into the spherical opening formed by the curved regions 446 of the teeth 442. The projections 448 provide a retaining surface for coupling the pivoting member 140 to the alignment arm 430, as shown in FIGS. 23 and 24. The pivoting member 140 is of the type described above with reference to FIGS. 11-22, which will not be described again here for brevity sake.

As shown in FIGS. 28 and 29, the guide portion 412 may include two arms 420 for engaging the two locking openings 230 of the base portion 212. The arms 420 may include a base 422 coupled to the guide portion 412, a recessed region 424 extending away from the base portion 422, and a locking projection 426 extending away from the recessed region 424. The locking projections 426 having a diameter or size larger than a diameter or size of the recessed region 424. The arms 420 are configured to engage the locking openings 230 in the base portion 212. When the arms 420 are inserted into the locking openings 230 of the base portion 212, the arms 420 may extend past the release buttons 232. The release buttons 232 may be of the type described above with reference to FIGS. 23-26 and 28 and will not be described again here for brevity sake. In addition, when the release buttons 232 are depressed, the openings (not shown) in the extension members 234 may be directly aligned with the locking openings 230 to allow for the arms 420 to be inserted through the openings in the extension members 234. During insertion, once the locking projections 426 pass through the openings (not shown) in the release buttons 232, the buttons 232 may be released and the extension members 234 may engage the recessed regions 424 to secure the guide portion 412 to the base portion 212. During removal of the guide portion 412, the release buttons 232 may be depressed to align the openings in the extension members 234 with the locking openings 230. Next, the guide portion 412 may be removed from the base portion 212 by pulling the guide portion 412 until the locking projections 426 pass through the openings (not shown) in the extension members 234 and out of the locking openings 230.

The compression device 260 may be of the type described above with reference to FIGS. 12-14, which will not be described again here for brevity sake. In addition, the engagement fastener 290, as shown in FIGS. 25-29, may be of the type described above with reference to FIGS. 11 and 19-21. Thus, the fixation guide 400 may be assembled in the same way as described above, which will not be described again here for brevity sake.

Figure 43:
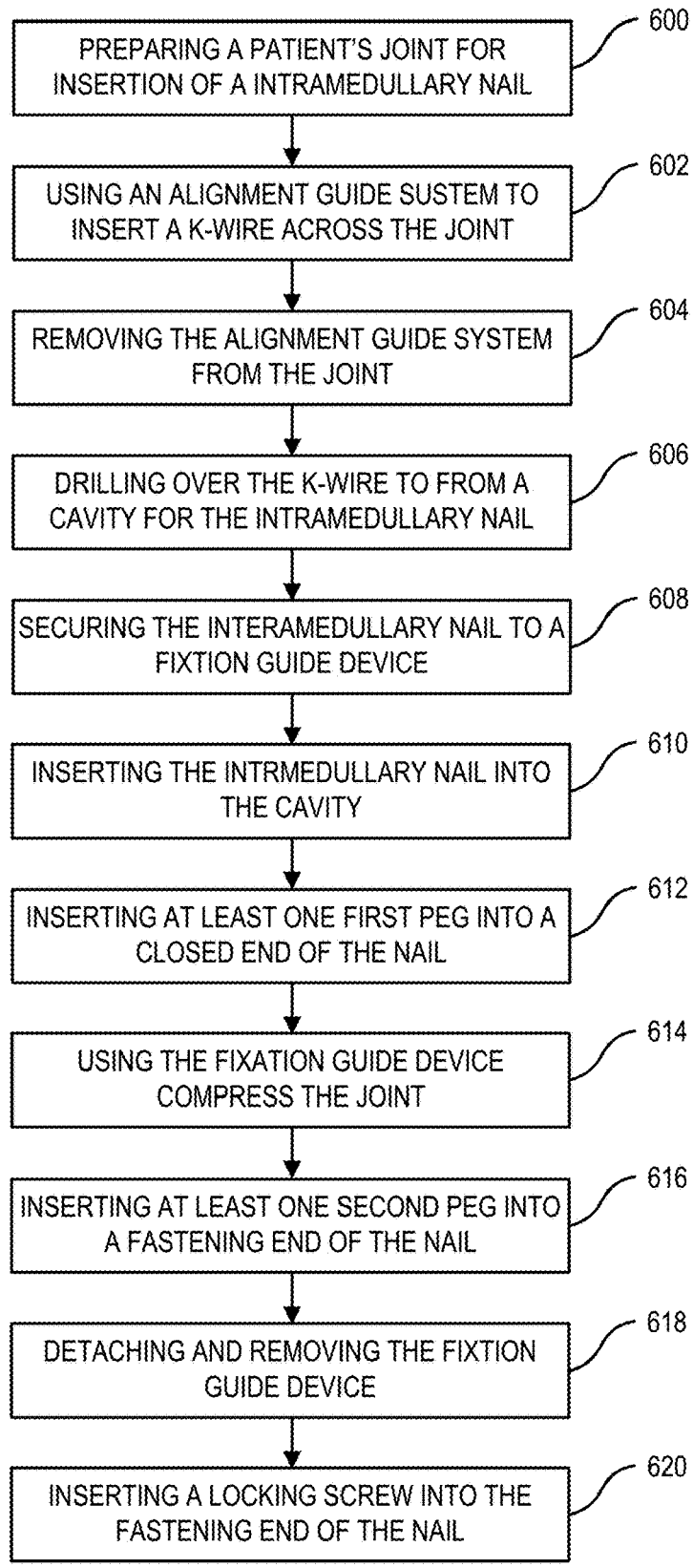
FIG. 43 depicts a method of inserting an intramedullary nail into a patient's foot, in accordance with an aspect of the present invention.

The surgical method for inserting an intramedullary nail 300 into a patient's foot 500 across a joint is shown in FIGS. 30-43. As shown in FIG. 43, the method may include preparing a patient's joint for insertion of an intramedullary nail 600. The method may also include using an alignment guide system to insert a k-wire across the patient's joint 602 and removing the alignment guide system from the joint 604. The method may further include drilling over the k-wire to form a cavity for the intramedullary nail 606 and securing the intramedullary nail to a fixation guide device 608. Next, the method may include inserting the intramedullary nail into the cavity 610 and inserting at least one first peg into a closed end of the intramedullary nail 612. In addition, the method may include using the fixation guide device to compression the joint 614 and inserting at least one second peg into a fixation end of the intramedullary nail 616. Further, the method may include detaching and removing the fixation guide device 618 and inserting a fastening screw into the fastening end of the intramedullary nail 620.

Figure 30:
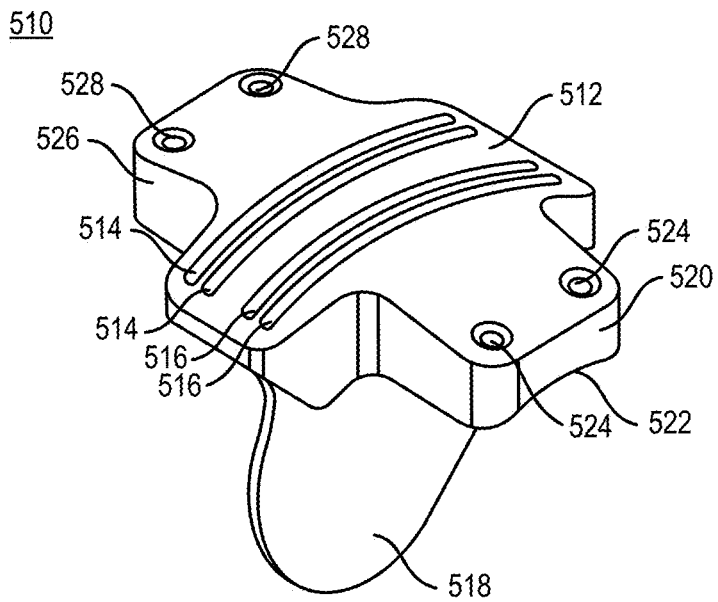
FIG. 30 is a perspective view of a cut guide, in accordance with an aspect of the present invention.

Referring now to FIGS. 30-42, the method may be described in greater detail. For example, the method may include making an incision over a joint, for example, a medial or dorsomedial incision over a first tarsometatarsal joint. Then, tissue dissection may be performed to expose the joint. Optionally, the cartilage may be resected and removed from the joint, then subchondral bone preparation may be performed. The cartilage resection may be performed, for example, using a cut guide 510, as shown in FIG. 30. The cut guide 510 may include a body or base member 512 The body 512 may include at least one first slot 514 on a first side of the body 512 and at least one second slot 516 on a second side of the body 512. The cut guide 510 may also include a fin or paddle 518 extending from a bottom surface of the body 512. The fin 518 is sized and shaped to fit into a joint between two bones, for example, the metatarsal and cuneiform bones. The bottom surface of the body 512 may be, for example, anatomically curved to mate with the surface of the dorsal surface of the patient's bones. The guide 510 may also include a first arm 520 extending from a first end of the body 512 and a second arm 526 extending from a second end of the body 512. The first arm 520 may extend in a proximal direction while the second arm 526 may extend in a distal direction. The first arm 520 may have a bottom surface 522, which may be anatomically curved to correspond to the patient's bones. The first arm 520 may also include at least one hole 524 for securing the cut guide 510 to a first bone for cutting a portion of the first bone. The second arm 526 may include at least one hole 528 for securing the cut guide 510 to a second bone for cutting a portion of the second bone. If a bone graft or implant (not shown) is needed to restore length to the patient's toe after the resection, the bone graft or implant (not shown) may then be inserted into the joint. The bone graft or implant (not shown) may be, for example, shaped to match the shape of the adjacent bones 502, 504.

Figure 31:
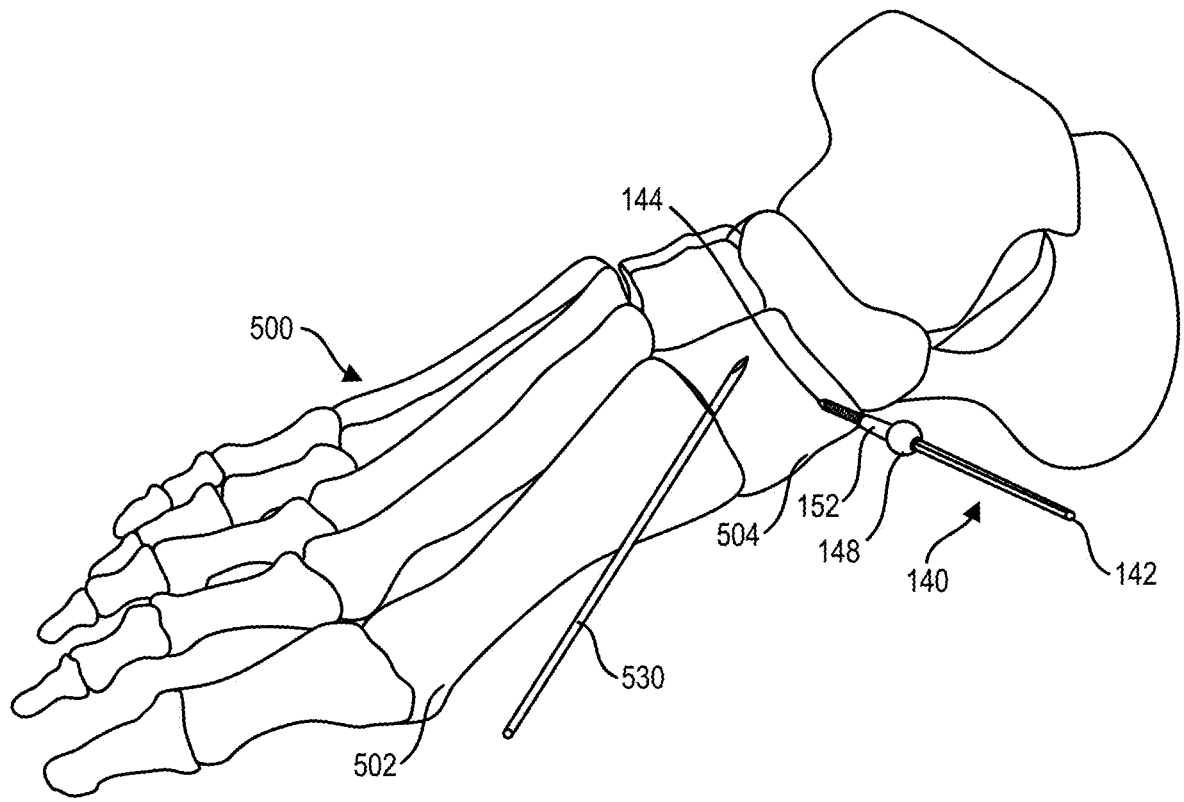
FIG. 31 is a perspective side view of a patient's foot with a k-wire and sphere wire, in accordance with an aspect of the present invention.

The method may also include inserting a k-wire 530, for example, through the metatarsal bone 502 and into the medial cuneiform bone 504 across the first tarsal-metatarsal joint, as shown in FIG. 31. The k-wire 530 may be placed from plantar medial distal to dorsal lateral proximal. Next, a pivoting member or sphere wire 140 may be obtained and placed at the proximal plantar medial aspect of the medial cuneiform 504, as shown in FIG. 31. Then, the pivoting end 130 of the alignment guide 108 may be coupled to the pivoting protrusion 148 of the pivoting member 140. Once coupled the alignment guide 108 may pivot about the pivoting protrusion 148 of the pivoting member 140.

Referring now to FIGS. 32A and 32B, an optional nail positioning guide 532 is shown. The nail positioning guide 532 may be used to assist with placement of a k-wire 180. The nail positioning guide 532 may include a base 534 and a handle 536 extending away from a top surface of the base 534 near the first end. The first end of the base 534 also includes a projection or leg 538 extending from a bottom surface of the base 534. The base 534 may also include at least one alignment opening 540 near the first end and an alignment marking 542 extending at least partially between the first end and the second end. The method may optionally include inserting the projection 538 into the central lateral aspect of the first tarsal-metatarsal joint. Once the projection 538 is inserted into the joint, the at least one alignment opening 540 is positioned on the patient's bone 502 at the desired start position for the k-wire 180. Next, a pilot hole may be formed in the patient's bone 502 through the at least one alignment opening 540 for appropriately lining up the k-wire for insertion.

Next, if not already coupled to the pivoting member 140, the alignment guide 108 may be coupled to the pivoting member 140, as shown in FIG. 33. A guide sleeve insert 160 may then be inserted into the first opening 116 in the distal end of the guide 108 and placed into contact with the patient's bone 502. The trajectory of the guide sleeve insert 160 is then aligned for the desired starting position of the k-wire 180, which matches the desired trajectory of the nail 300. If the nail positioning guide 532 was used, the distal end of the guide sleeve insert 160 may be aligned to the pivot hole in the bone 502. Specifically, the channel 170 of the guide sleeve insert 160 may be aligned over the pivot hole in the bone 502. Then, the k-wire 180 may be inserted through the guide sleeve insert 160 and into the patient's bone 502 until it contacts the pivoting protrusion 148 of the pivoting member 140 or reaches the proximal plantar aspect of the medial cuneiform 504. Placement of the k-wire 180 may then be confirmed using fluoroscopy. Once the desired placement of the k-wire 180 is achieved, the sleeve insert 160 may be removed from the k-wire 180 and guide 108 removed from the pivoting member 140. After the sleeve insert 160 and guide 108 are removed, the length of the k-wire 180 may be measures with a nail depth gauge (not shown).

Figure 34:
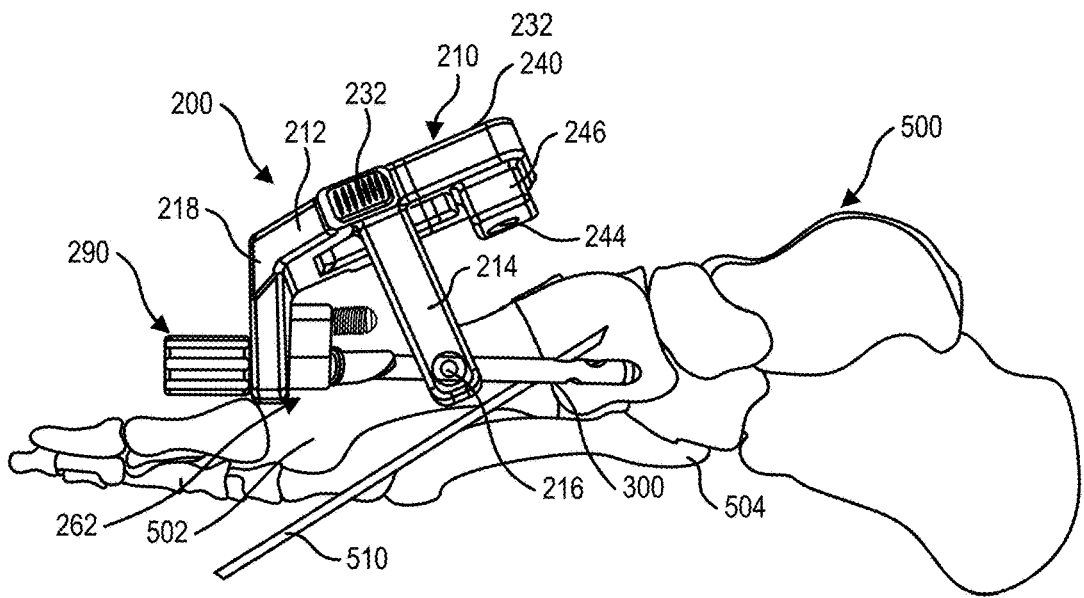
FIG. 34 is a perspective side view of the embodiment of FIG. 33 with an intramedullary nail inserted into the patient's foot and coupled to a fixation guide, in accordance with an aspect of the present invention.

A cannulated drill bit (not shown) of a drill may then be inserted over the k-wire 180 and drilled into the bones 502, 504 until the pivoting member 140 is contacted. Once an opening is drilled over the k-wire 180, the pivoting member 140 may be removed from the patient's bone 504. Next, a fixation guide 200 may be obtained and assembled including selecting and attaching a guide portion 240 that corresponds to the measured size of the inserted nail 300. The nail 300 may also be coupled to the fixation guide 200. The engagement fastener 290 is then inserted into the guide 210 and coupled to the selected nail 300. The nail 300 may be coupled to the guide 210 by turning the engagement fastener 290 in a clockwise direction to thread the engagement fastener 290 into the inside of the nail 300. Then the assembled alignment guide 108 may be inserted into the drilled hole, as shown in FIG. 34. The nail 300 may be inserted until the contoured piece on the frame 210 is flush with the dorsal aspect of the first metatarsal. Fluoroscopy may then be used to confirm the size of the nail 300 and the placement of the nail. The pivoting member 140 may then be removed.

Figure 35:
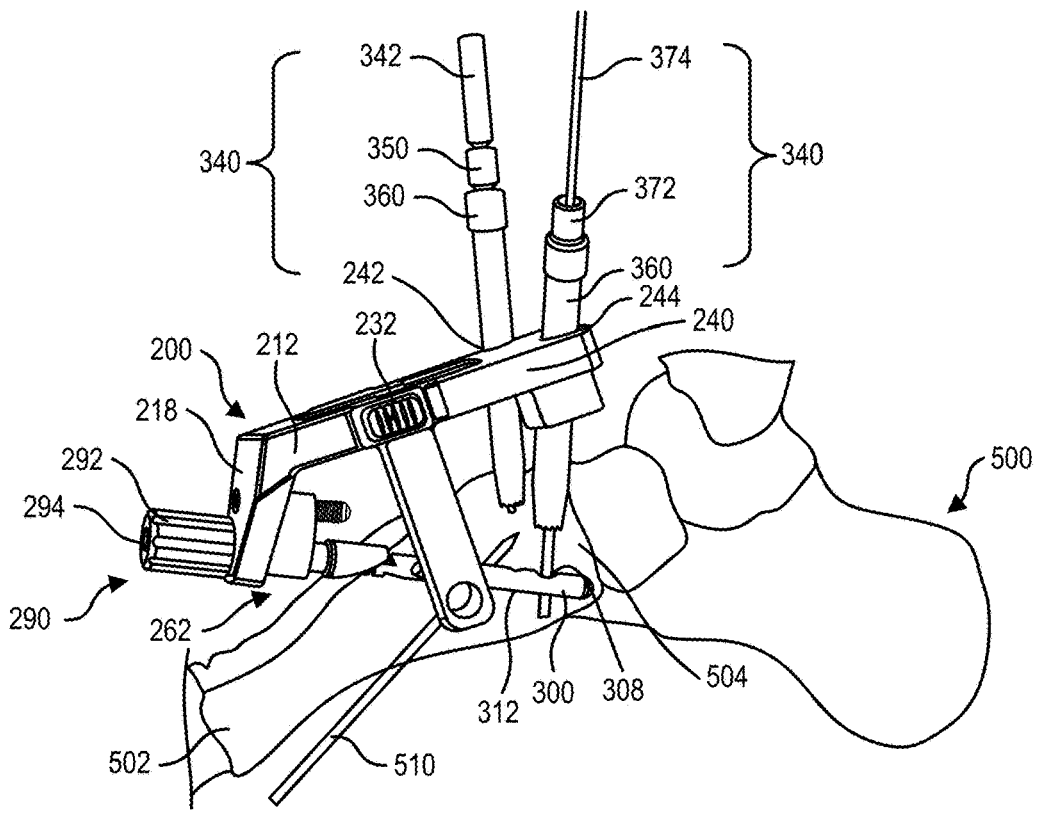
FIG. 35 is a perspective side view of the embodiment of FIG. 34 with the fixation guide system coupled to the patient's foot, in accordance with an aspect of the present invention.
Figure 36:
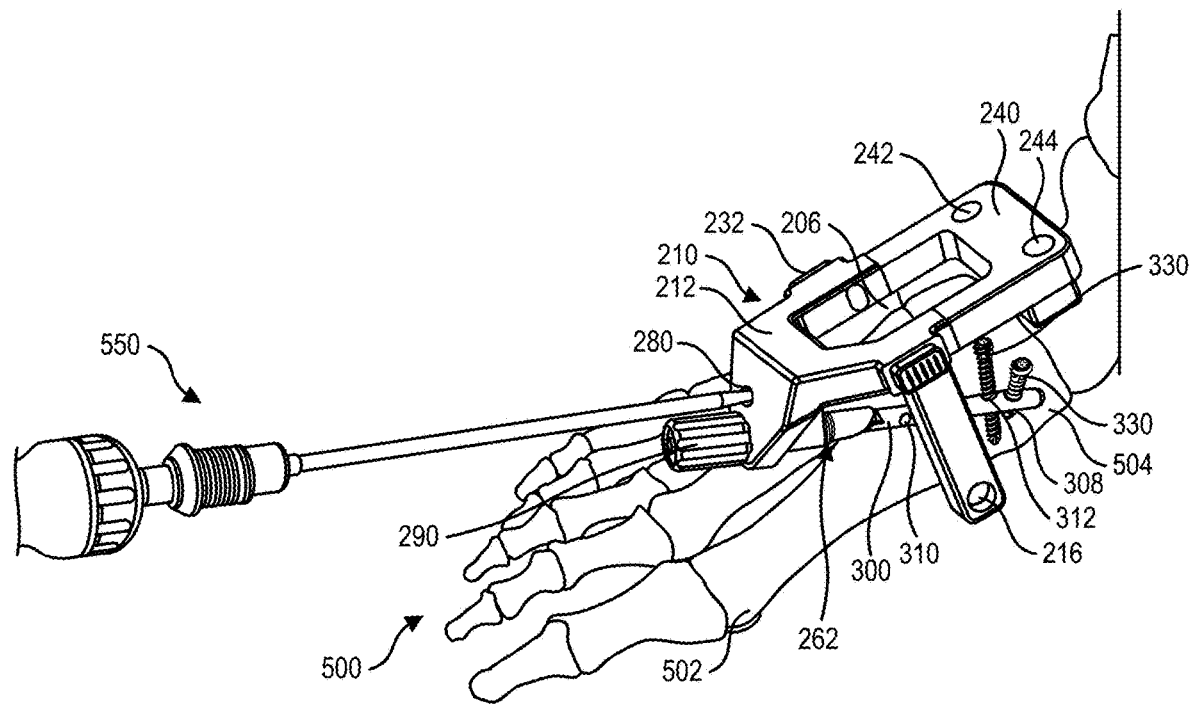
FIG. 36 is a perspective top view of the embodiment of FIG. 35 with screw driver, in accordance with an aspect of the present invention.

Referring now to FIGS. 11 and 35, an obturator 342 may be inserted into the drill guide 350 and the drill guide 350 may be inserted into a screw guide 360. The assembled guide system 340 may then be inserted into the second drill hole 242, as shown in FIG. 35. A pin guide system 370 may then be inserted into the third drill hole 244. The pin guide system 370 may include a screw guide 360, a k-wire guide 372 sized to fit inside of the screw guide 360, and a k-wire 374 sized to fit within the k-wire guide 372. The k-wire 374 may be inserted through the k-wire guide 372, into the patient's bone 504 and through an opening 308 in the nail 300, as shown in FIG. 35. Next, the obturator 342 may be removed from the drill guide 350 and a drill bit (not shown) or k-wire drill may be inserted through the drill guide 350 to drill into the patient's bone 504. Then, the drill guide 350 may be removed from the screw guide 360 and a depth gauge (not shown) is inserted through the screw guide 360 to measure for selecting a first threaded peg 330. The selected threaded peg 330 may then be inserted through the screw guide 360 into the bone 504 through the opening 312 in the nail 300, as shown in FIG. 36. After the threaded peg 330 is inserted the screw guide 360 may be removed from the fixation guide 200.

Next, the k-wire 374 and k-wire guide 372 may be removed from the screw guide 360 in the third drill hole 244. A drill guide (not shown), such as guide 350, may then be inserted into the screw guide 360. A drill bit (not shown) may then be inserted through the drill guide (not shown) to drill into the patient's bone 504. The drill guide (not shown) may then be removed from the screw guide 360 and depth gauge (not shown) may be inserted through the screw guide 360 to measure for selecting a second threaded peg 330. The selected threaded peg 330 may be inserted through the screw guide 360 into the bone 504 through the opening 308 in the nail 300, as shown in FIG. 36. Once the threaded pegs 330 are inserted through the nail openings 308, 312, the screw guides 360 may be removed from the second and third drill holes 242, 244. Then, the temporary fixator or k-wire 510 may be removed from across the joint.

Figure 37:
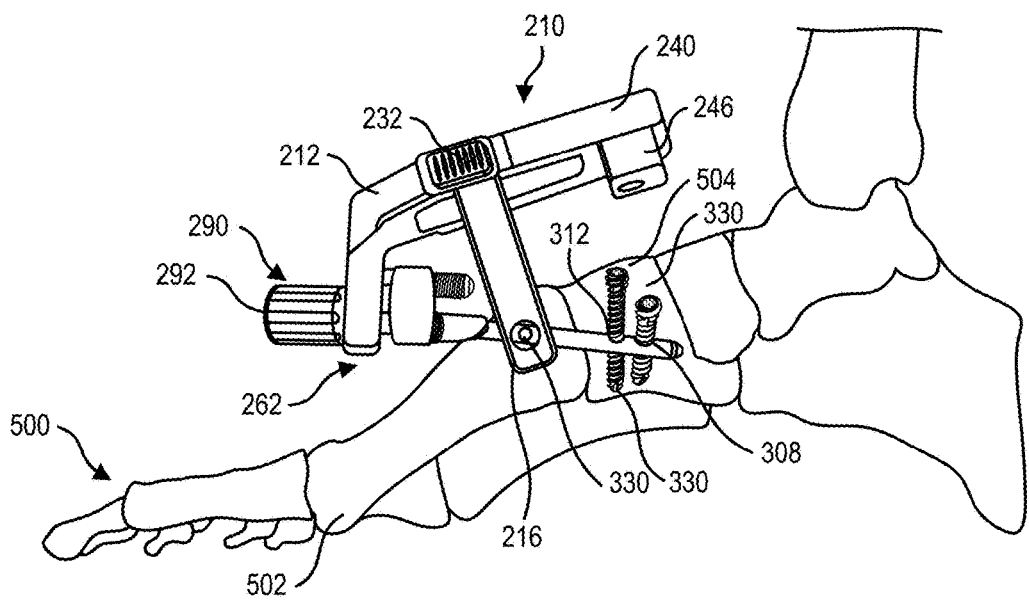
FIG. 37 is a perspective side view of the embodiment of FIG. 36 showing the threaded pegs being inserted through the intramedullary nail, in accordance with an aspect of the present invention.

With continued reference to FIG. 36, a solid driver 550 may be used to tighten the bolt 280 of the fixation guide 200 to translate the compression member 262 creating compression across the arthrodesis site. Compression is created between the medial cuneiform bone 504 secured to the nail 300 with pegs 330 and the compression member 262 contacting and translating the metatarsal bone 502 into closer contact with the medial cuneiform bone 504, as shown in FIG. 37. The compression member 262 pushes the metatarsal bone 502 into contact with the medial cuneiform bone 504 along the longitudinal axis of the nail 300. The compression device 260 provides controlled compression across the fusion joint to produce the proper surface contact stress between the metatarsal bone 502 and medial cuneiform bone 504 to promote osteosynthesis and enable proper healing. The protrusion 270 of the compression device 260 includes a convex surface for applying a central axis force and contact compression to bones having different topographical morphologies of bone. The end of the protrusion 270 is angled for oblique contact with the patient's bone and the teeth or textured surface 278 provide a gripping surface to assist with gripping the bone during compression of the joint.

Figure 38:
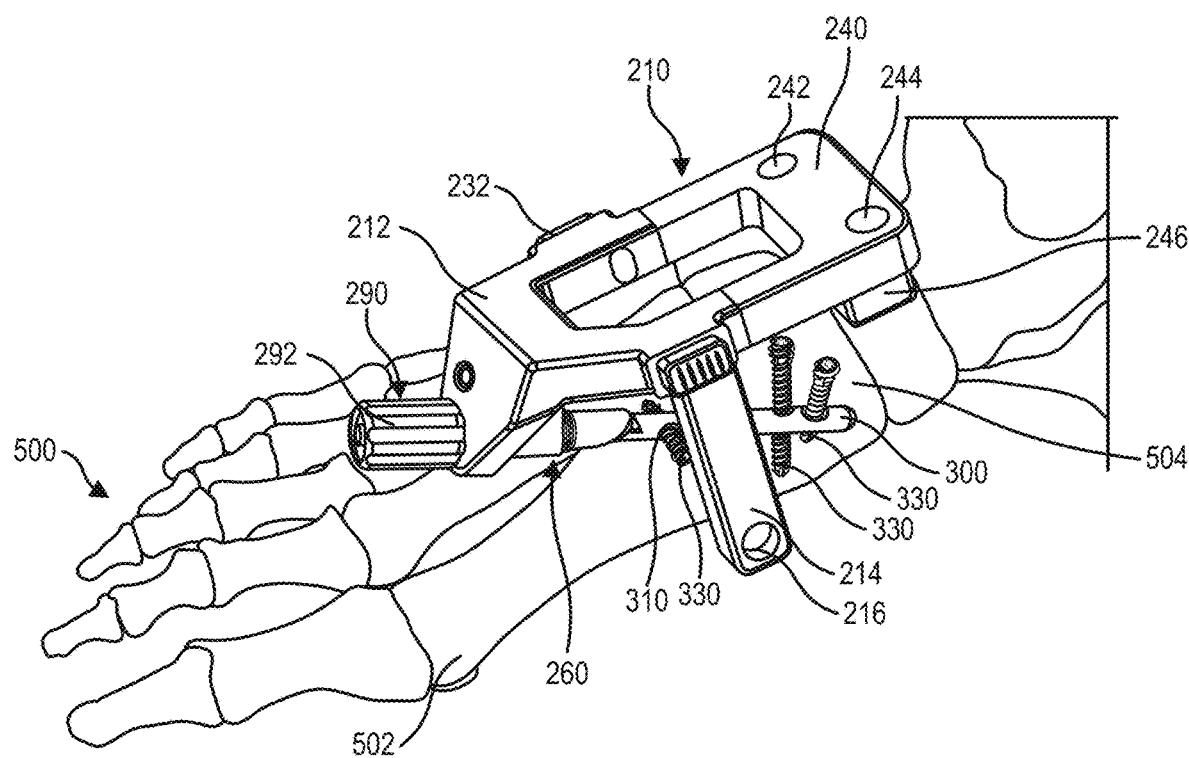
FIG. 38 is a perspective top view of the embodiment of FIG. 37 showing all the threaded pegs inserted through the intramedullary nail, in accordance with an aspect of the present invention.

Once the desired compression is achieved across the joint, a third peg 330 may be inserted through the nail opening 310, as shown in FIG. 37. The third peg 330 may be inserted by, for example, inserting a coupled obturator 342, drill guide 350 and screw guide 360 through the first drill hole 216 of the fixation guide 200. The obturator 342 may then be removed from the drill guide 350 and a drill bit (not shown) may be inserted through the drill guide 350 to drill into the patient's bone 502. Then, the drill guide 350 may be removed from the screw guide 360 and a depth gauge (not shown) may be inserted through the screw guide 360 to measure for selecting the third threaded peg 330. The selected threaded peg 330 may then be inserted through the screw guide 360 into the bone 502 through the opening 310 in the nail 300, as shown in FIGS. 37 and 38. After the threaded peg 330 is inserted the screw guide 360 may be removed from the fixation guide 200.

Figure 39:
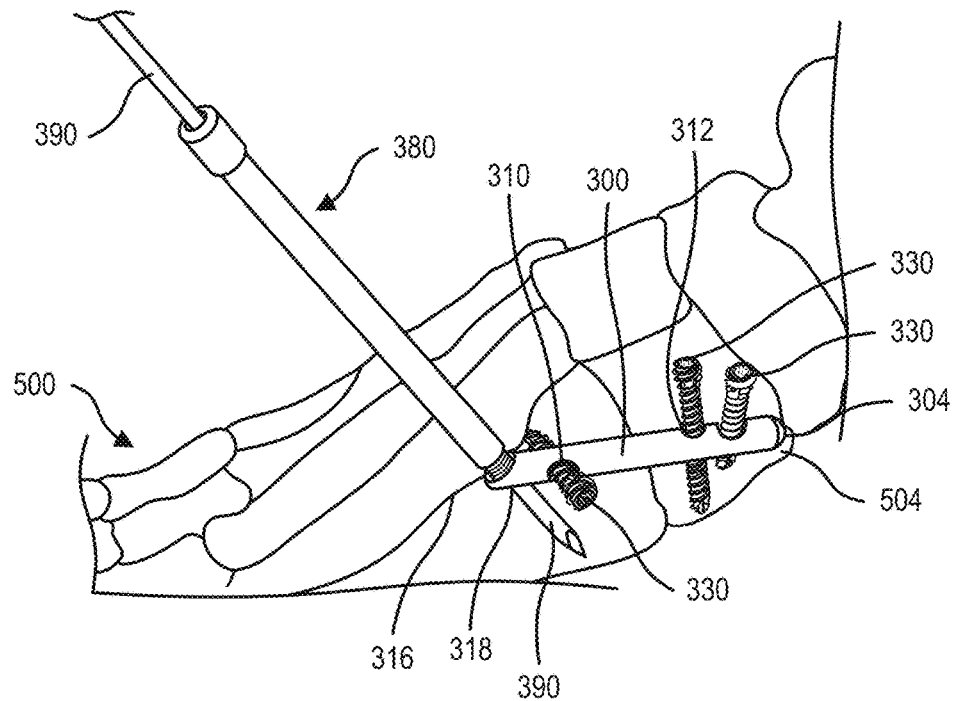
FIG. 39 is a side perspective view of the embodiment of FIG. 38 showing insertion of the locking screw through the intramedullary nail, in accordance with an aspect of the present invention.
Figure 40:
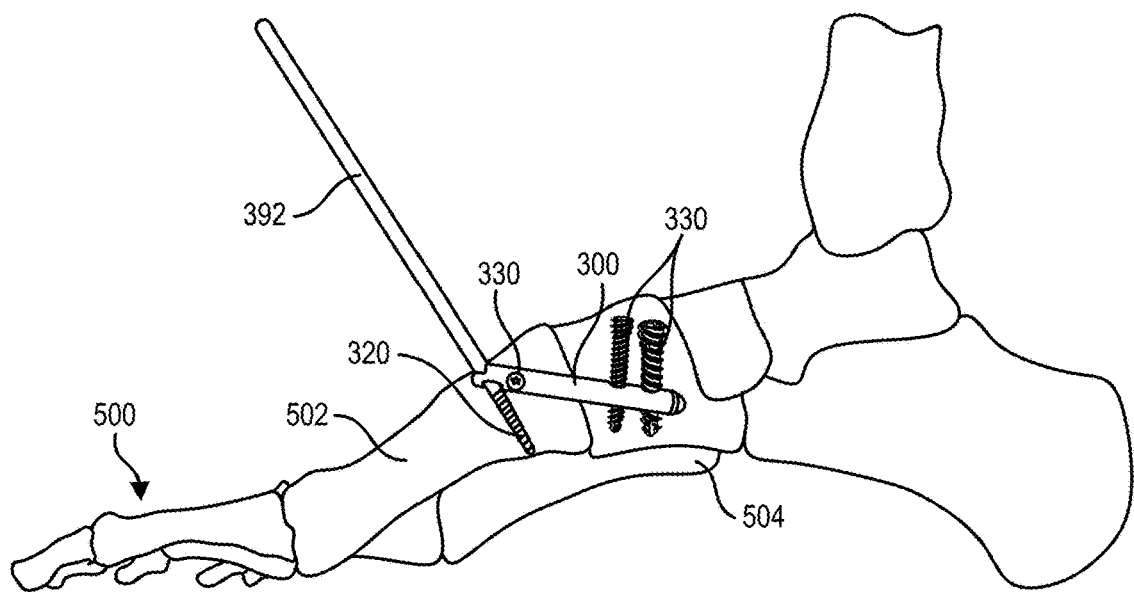
FIG. 40 is a side view of the embodiment of FIG. 39 after removal of the fixation guide, in accordance with an aspect of the present invention.

Next, as shown in FIG. 39, the fixation guide 200 may be removed from the patient's foot 500. The fixation guide 200 may be removed by turning the knob 292 of the engagement fastener 290. As the knob 292 is turned counterclockwise, the threaded portion 298 of the engagement fastener 290 disengages the insertion opening 316 in the nail 300. Then, the fixation guide 200 may be removed from the patient's foot 500, as shown in FIG. 39. Next, a locking guide 380 may be placed into the insertion opening 316 of the nail 300, as shown in FIG. 39. A drill bit or k-wire drill 390 may then be used to drill an opening through the metatarsal 502. A depth gauge (not shown) may be inserted through the locking guide 380 to measure the size locking screw 320 needed, as shown in FIG. 39. Then, the depth gauge (not shown) and locking guide 380 may be removed and the locking screw 320 may be inserted through the nail opening 318 using a driver 392, as shown in FIG. 40. The locking screw 320 is inserted into the metatarsal 502 and the placement and size are then confirmed using fluoroscopy.

Figure 41:
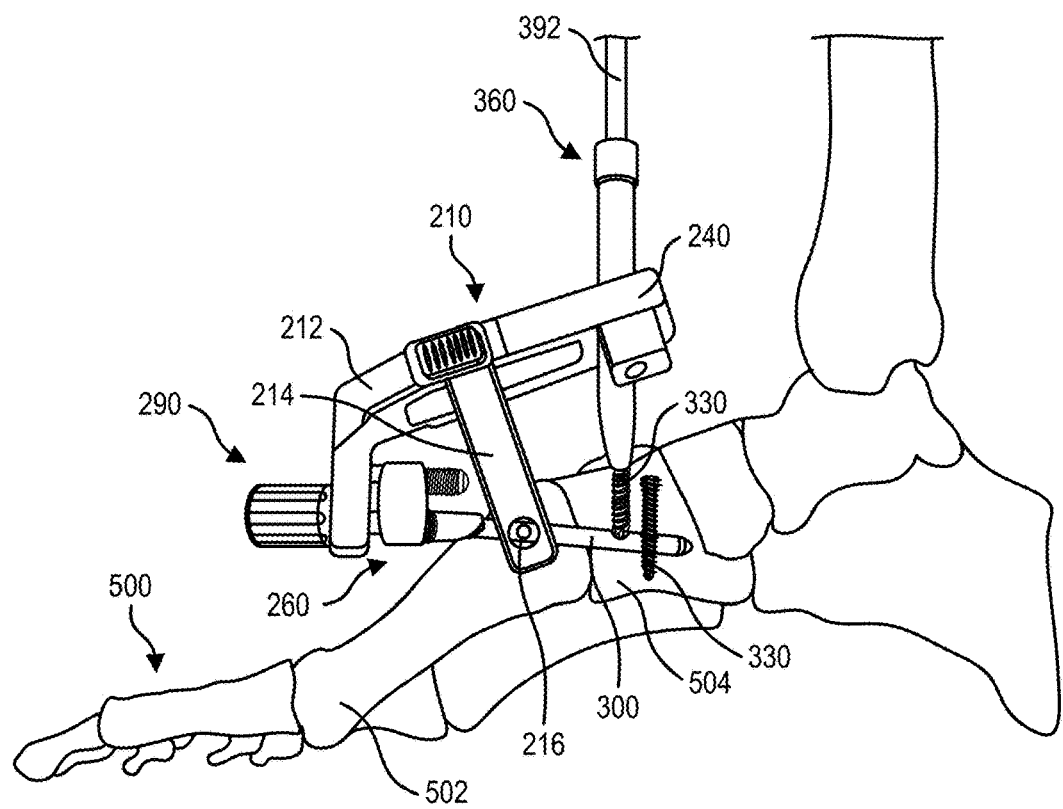
FIG. 41 is a side view of the embodiment of FIG. 40 showing the fixation guide coupled to the intramedullary nail for removal of the nail from the patient's foot, in accordance with an aspect of the present invention.
Figure 42:
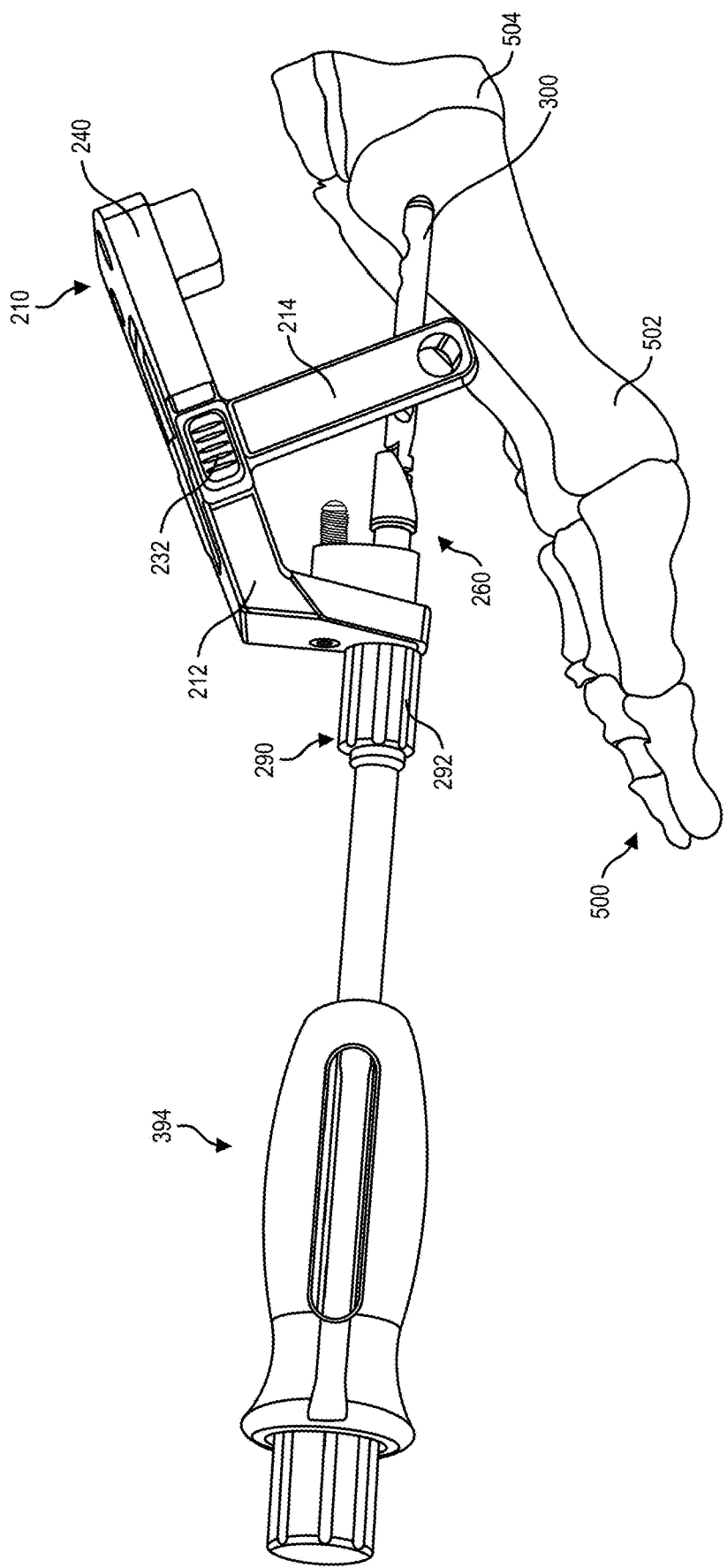
FIG. 42 is a side view of the embodiment of FIG. 41 showing the intramedullary nail and the fixation guide being removed from the patient's foot, in accordance with an aspect of the present invention.

The method may further include a removal or revision procedure. The removal procedure may include removing the locking screw 320 from the intramedullary nail 300 using the driver 392, as shown in FIG. 40. Next, a fixation guide 200 may be selected include the guide portion 240 that corresponds to the nail 300 being removed. The frame 210 of the fixation guide 200 may be coupled to the nail 300 and the guide portion 240 may be inserted and locked to the frame 210, as shown in FIG. 41. An engagement fastener 290 may then be inserted into the frame 210 and turned to thread into the insertion opening 316 in the nail 300. Once the fixation guide 200 is secured to the nail 300, a screw guide 360 may be inserted into the second drill hole 242, as shown in FIG. 41. A driver 392 may then be inserted into the cannulation 366 of the screw guide 360 and inserted into the head of the first peg 330. The driver 392 may be rotated to remove the first peg 330 from the nail opening 312 and out through the screw guide 360. Next, the screw guide 360 may be removed from the second drill hole 242 and inserted into the third drill hole 244. The driver 392 may then be inserted through the screw guide 360 and inserted into the head of the second peg 330. Next, the second peg 330 may be removed from the nail opening 308 and out through the screw guide 360. The screw guide 360 may then be removed from the third drill hole 244 and inserted into the first drill hole 216. The driver 392 may then be inserted through the screw guide 360 and inserted into the head of the third peg 330. Next, the third peg 330 may be removed from the nail opening 310 and out through the screw guide 360. Finally, a slaphammer 394 may be attached to the engagement fastener 290 of the fixation guide 200. Then the slaphammer 394 may be used to back the nail 300 out of the patient's foot 500.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

What is claimed is:

1. An intramedullary nail, comprising:
   a body, comprising:
      a closed end at a first end; and
      a fastening end at a second end, the fastening end comprising:
         a first fastening segment with a first length and positioned on a bottom of the body; and
         a second fastening segment with a second length and positioned on a top of the body, wherein the first length is longer than the second length, and wherein the second fastening segment has an angled engagement surface relative to a surface of the fastening end and extending into the body from the second end toward the first end; and
      at least two openings extending into a side of the body, wherein the at least two openings are disposed on independent planes and angularly spaced apart from each other.

2. The intramedullary nail of claim 1, wherein the fastening end comprises:
   an insertion opening extending into the body along a longitudinal axis of the intramedullary nail from the second end; and
   an engagement opening extending into the body of the intramedullary nail transverse to the longitudinal axis of the intramedullary nail.

3. The intramedullary nail of claim 2, wherein the insertion opening extends through the first fastening segment and the second fastening segment.

4. The intramedullary nail of claim 3, wherein the engagement opening extends through the first fastening segment.

5. The intramedullary nail of claim 4, wherein the engagement opening extends through the body adjacent to the second fastening segment.

6. The intramedullary nail of claim 1, wherein the first fastening segment has a first end at the fastening end and a second end where the first fastening segment engages the second fastening segment, wherein the angled engagement surface of the second fastening segment has a first end at the fastening end and a second end where the second fastening segment engages the first fastening segment, and wherein the second end of the first fastening segment is positioned closer to the closed end of the intramedullary nail than the first end of the second fastening segment.

7. A compression system, comprising:
an intramedullary nail, comprising:
a body, comprising:
a closed end at a first end; and
a fastening end at a second end, the fastening end comprising:
a first fastening segment with a first length and positioned on a bottom of the body; and
a second fastening segment with a second length and positioned on a top of the body, wherein the first length is longer than the second length, and wherein the second fastening segment has an angled engagement surface relative to a surface of the fastening end and extending into the body from the second end toward the first end; and
at least two openings extending into a side of the body, wherein the at least two openings are disposed on independent planes and angularly spaced apart from each other; and
a compression device for engaging the intramedullary nail.

8. The compression system of claim 7, wherein the fastening end comprises:
an insertion opening extending into the body along a longitudinal axis of the intramedullary nail from the second end; and
an engagement opening extending into the body of the intramedullary nail transverse to the longitudinal axis of the intramedullary nail.

9. The compression system of claim 8, wherein the compression device comprises:
a compression member configured to engage the fastening end of the intramedullary nail, wherein the compression member comprises:
a base with a top end and a bottom end; and
a protrusion extending away from a first side at the bottom end of the base, wherein a bottom surface of the protrusion is angled from a point between a top and a midline of the protrusion to a position near a midpoint of a bottom end of the protrusion along a longitudinal axis of the protrusion.

10. The compression system of claim 9, wherein the compression member further comprises:
a first opening positioned near the top end and proximal to the protrusion, wherein the first opening receives a bolt; and
a second opening positioned near the bottom end and extending through the protrusion.

11. The compression system of claim 10, wherein the compression member further comprises:
an engagement fastener extending through the compression member and engaging the insertion opening of the intramedullary nail, wherein the engagement fastener comprises:
a knob at a first end;
a shaft extending away from the knob to a second end; and
a threaded end for coupling to the intramedullary nail.

* * * * *